(12) United States Patent
Martinelli et al.

(10) Patent No.: US 6,701,179 B1
(45) Date of Patent: Mar. 2, 2004

(54) COIL STRUCTURES AND METHODS FOR GENERATING MAGNETIC FIELDS

(76) Inventors: Michael A. Martinelli, 58 Wedgemere Ave., Winchester, MA (US) 01890; Brad Jascob, 11580 Marshall St., Broomfield, CO (US) 80020; Mark W. Hunter, 204 Summit Trail, Broomfield, CO (US) 80020

( * ) Notice: Subject to any disclaimer, the term of this patent is extended or adjusted under 35 U.S.C. 154(b) by 234 days.

(21) Appl. No.: 09/698,896

(22) Filed: Oct. 27, 2000

Related U.S. Application Data

(60) Provisional application No. 60/161,990, filed on Oct. 28, 1999.

(51) Int. Cl.$^7$ .................................................. A61B 5/05
(52) U.S. Cl. ....................................... 600/424; 606/130
(58) Field of Search .............................. 600/407, 424, 600/410, 422; 128/899; 324/207.11, 207.12, 207.13, 207.22

(56) References Cited

U.S. PATENT DOCUMENTS

| | | | |
|---|---|---|---|
| 3,674,014 A | 7/1972 | Tillander | 128/2.05 |
| 3,868,565 A | 2/1975 | Kuipers | 324/41 |
| 4,054,881 A | 10/1977 | Raab | 343/112 |
| 4,173,228 A | 11/1979 | Van Steenwyk et al. | 128/653 |
| 4,262,306 A | 4/1981 | Renner | 358/93 |
| 4,287,809 A | 9/1981 | Egli et al. | 89/41 |
| 4,314,251 A | 2/1982 | Raab | 343/112 |
| 4,317,078 A | 2/1982 | Weed et al. | 324/208 |
| 4,339,953 A | 7/1982 | Iwasaki | 73/654 |
| 4,396,885 A | 8/1983 | Constant | 324/208 |
| 4,422,041 A | 12/1983 | Lienau | 324/207 |
| 4,431,005 A | 2/1984 | McCormick | 128/656 |
| 4,572,198 A | 2/1986 | Codrington | 128/653 |
| 4,613,866 A | 9/1986 | Blood | 343/448 |
| 4,618,978 A | 10/1986 | Cosman | 378/164 |
| 4,642,786 A | 2/1987 | Hansen | 364/559 |
| 4,649,504 A | 3/1987 | Krouglicof et al. | 364/559 |
| 4,737,794 A | 4/1988 | Jones | 342/448 |
| 4,821,731 A | 4/1989 | Martinelli et al. | 128/662.06 |
| 4,836,778 A | 6/1989 | Baumrind et al. | 433/69 |
| 4,849,692 A | 7/1989 | Blood | 324/208 |
| 4,905,698 A | 3/1990 | Strohl, Jr. et al. | 128/653 |
| 4,945,305 A | 7/1990 | Blood | 324/207 |
| 4,977,655 A | 12/1990 | Martinelli | 29/25.35 |
| 4,989,608 A | 2/1991 | Ratner | 128/653 |

FOREIGN PATENT DOCUMENTS

| | | |
|---|---|---|
| EP | 0419729 A1 | 9/1989 |
| EP | 0655138 B1 | 8/1993 |
| EP | 0894473 A2 | 1/1995 |
| WO | WO 91/07726 | 5/1991 |
| WO | WO 92/06645 | 4/1992 |
| WO | WO 94/04938 | 3/1994 |

OTHER PUBLICATIONS

Edward C. Benzel et al., "Magnetic Source Imaging: a Review of the Magnes System of Biomagnetic Technologies Incorporated," Nurosurgery, vol. 33, No. 2 (Aug. 1993), p.252–259.

Primary Examiner—George Manuel
Assistant Examiner—Runa Shah Qaderi
(74) Attorney, Agent, or Firm—Harness, Dickey & Pierce, P.L.C.

(57) ABSTRACT

An apparatus for determining a location of a sensor in a surgical navigation domain includes a first magnetic field generator having a first coil set, a second magnetic field generator having a second coil set. The first and second coil sets are disposed substantially within a common plane. The apparatus further includes a processor configured to receive a plurality of signals. The processor calculates the location of the sensor from the plurality of signals. The sensor produces the plurality of signals in response to magnetic fields generated by the first and second magnetic field generators.

31 Claims, 28 Drawing Sheets

U.S. PATENT DOCUMENTS

| | | | | |
|---|---|---|---|---|
| 4,991,579 A | 2/1991 | Allen | 128/653 |
| 5,002,058 A | 3/1991 | Martinelli | 128/662 |
| 5,005,592 A | 4/1991 | Cartmell | 128/899 |
| 5,016,639 A | 5/1991 | Allen | 128/653 |
| 5,042,486 A | 8/1991 | Pfeiler et al. | 128/653 |
| 5,050,608 A | 9/1991 | Watanabe et al. | 128/653 |
| 5,054,492 A | 10/1991 | Scribner et al. | 128/662.06 |
| 5,059,789 A | 10/1991 | Salcudean | 250/206.1 |
| 5,086,401 A | 2/1992 | Glassman et al. | 395/94 |
| 5,099,845 A | 3/1992 | Besz et al. | 128/653.1 |
| 5,105,829 A | 4/1992 | Fabian et al. | 128/899 |
| 5,152,288 A | 10/1992 | Hoenig et al. | 128/653.1 |
| 5,161,536 A | 11/1992 | Vilkomerson et al. | 128/660.07 |
| 5,187,475 A | 2/1993 | Wagener et al. | 340/870.32 |
| 5,197,476 A | 3/1993 | Nowacki et al. | 128/660.03 |
| 5,198,768 A | 3/1993 | Keren | 324/318 |
| 5,198,877 A | 3/1993 | Schulz | 356/375 |
| 5,211,164 A | 5/1993 | Allen | 128/653.1 |
| 5,211,165 A | 5/1993 | Dumoulin et al. | 128/653.1 |
| 5,214,615 A | 5/1993 | Bauer | 367/128 |
| 5,222,499 A | 6/1993 | Allen et al. | 128/653.1 |
| 5,228,442 A | 7/1993 | Imran | 128/642 |
| 5,249,581 A | 10/1993 | Horbal et al. | 128/664 |
| 5,251,635 A | 10/1993 | Dumoulin et al. | 128/653.2 |
| 5,253,647 A | 10/1993 | Takahashi et al. | 128/653.1 |
| 5,255,680 A | 10/1993 | Darrow et al. | 128/653.1 |
| 5,257,636 A | 11/1993 | White | 128/897 |
| 5,265,610 A | 11/1993 | Darrow et al. | 128/653.1 |
| 5,265,611 A | 11/1993 | Hoenig et al. | 128/653.1 |
| 5,269,759 A | 12/1993 | Hernandez et al. | 604/96 |
| 5,271,400 A | 12/1993 | Dumoulin et al. | 128/653.2 |
| 5,273,025 A | 12/1993 | Sakiyama et al. | 128/6 |
| 5,274,551 A | 12/1993 | Corby, Jr. | 364/413.13 |
| 5,279,309 A | 1/1994 | Taylor et al. | 128/782 |
| 5,295,483 A | 3/1994 | Nowacki et al. | 128/660.03 |
| 5,299,254 A | 3/1994 | Dancer et al. | 378/163 |
| 5,299,288 A | 3/1994 | Glassman et al. | 395/80 |
| 5,309,913 A | 5/1994 | Kormos et al. | 128/653.1 |
| 5,315,630 A | 5/1994 | Sturm et al. | 378/64 |
| 5,316,024 A | 5/1994 | Hirschi et al. | 128/899 |
| 5,318,025 A | 6/1994 | Dumoulin et al. | 128/653.2 |
| 5,325,873 A | 7/1994 | Hirschi et al. | 128/899 |
| 5,353,795 A | 10/1994 | Souza et al. | 128/653.2 |
| 5,368,030 A | 11/1994 | Zinreiche et al. | 128/653.1 |
| 5,375,596 A | 12/1994 | Twiss et al. | 128/653.1 |
| 5,377,678 A | 1/1995 | Dumoulin et al. | 128/653.1 |
| 5,383,454 A | 1/1995 | Bucholz | 128/653.1 |
| 5,386,828 A | 2/1995 | Owens et al. | 128/653.1 |
| 5,389,101 A | 2/1995 | Heilbrun et al. | 606/130 |
| 5,391,199 A | 2/1995 | Ben-Haim | 607/122 |
| 5,402,801 A | 4/1995 | Taylor | 128/898 |
| 5,408,409 A | 4/1995 | Glassman et al. | 364/413.13 |
| 5,417,210 A | 5/1995 | Funda et al. | 128/653.1 |
| 5,419,325 A | 5/1995 | Dumoulin et al. | 128/653.2 |
| 5,425,367 A | 6/1995 | Shapiro et al. | 128/653.1 |
| 5,425,382 A | 6/1995 | Golden et al. | 128/899 |
| 5,429,132 A | 7/1995 | Guy et al. | 128/653.1 |
| 5,437,277 A | 8/1995 | Dumoulin et al. | 128/653.1 |
| 5,443,066 A | 8/1995 | Dumoulin et al. | 128/653.1 |
| 5,443,489 A | 8/1995 | Ben-Haim | 607/115 |
| 5,445,144 A | 8/1995 | Wodicka et al. | 128/207.14 |
| 5,445,150 A | 8/1995 | Dumoulin et al. | 128/653.1 |
| 5,445,166 A | 8/1995 | Taylor | 128/897 |
| 5,453,686 A | 9/1995 | Anderson | 324/207.17 |
| 5,456,718 A | 10/1995 | Szymaitis | 623/11 |
| 5,480,422 A | 1/1996 | Ben-Haim | 607/122 |
| 5,483,961 A | 1/1996 | Kelly et al. | 128/653.1 |
| 5,487,729 A | 1/1996 | Avellanet et al. | 604/96 |
| 5,513,637 A | 5/1996 | Twiss et al. | 128/653.1 |
| 5,517,990 A | 5/1996 | Kalfas et al. | 128/653.1 |
| 5,542,938 A | 8/1996 | Avellanet et al. | 604/280 |
| 5,546,951 A | 8/1996 | Ben-Haim | 128/702 |
| 5,558,091 A | 9/1996 | Acker et al. | 128/653.1 |
| 5,568,809 A | 10/1996 | Ben-Haim | 128/656 |
| 5,572,999 A | 11/1996 | Taylor et al. | 128/653.1 |
| 5,588,430 A | 12/1996 | Bova et al. | 128/653.1 |
| 5,592,939 A | 1/1997 | Martinelli | 128/653.1 |
| 5,600,330 A | 2/1997 | Blood | 342/463 |
| 5,603,318 A | 2/1997 | Heilbrun et al. | 128/630 |
| 5,617,857 A | 4/1997 | Chader et al. | 128/653.1 |
| 5,622,169 A | 4/1997 | Golden et al. | 128/653.1 |
| 5,622,170 A | 4/1997 | Schulz | 128/653.1 |
| 5,630,431 A | 5/1997 | Taylor | 128/897 |
| 5,640,170 A | 6/1997 | Anderson | 343/895 |
| 5,645,065 A | 7/1997 | Shapiro et al. | 128/653.1 |
| 5,647,361 A | 7/1997 | Damadian | 128/683.2 |
| 5,662,111 A | 9/1997 | Cosman | 128/653.1 |
| 5,676,673 A | 10/1997 | Ferre et al. | 606/130 |
| 5,694,945 A | 12/1997 | Ben-Haim | 128/736 |
| 5,695,500 A | 12/1997 | Taylor et al. | 606/130 |
| 5,711,299 A | 1/1998 | Manwaring et al. | 128/653.1 |
| 5,713,946 A | 2/1998 | Ben-Haim | 607/122 |
| 5,718,241 A | 2/1998 | Ben-Haim et al. | 128/702 |
| 5,729,129 A | 3/1998 | Acker | 324/207.12 |
| 5,730,129 A | 3/1998 | Darrow et al. | 128/653.1 |
| 5,732,703 A | 3/1998 | Kalfas et al. | 128/653.1 |
| 5,738,096 A | 4/1998 | Ben-Haim | 128/653.1 |
| 5,749,362 A | 5/1998 | Funda et al. | 128/653.1 |
| 5,752,513 A | 5/1998 | Acker et al. | 128/653.1 |
| 5,758,667 A | 6/1998 | Slettenmark | 128/899 |
| 5,762,064 A | 6/1998 | Polvani | 128/653.1 |
| 5,776,064 A | 7/1998 | Kalfas et al. | 600/414 |
| 5,787,886 A | 8/1998 | Kelly et al. | 128/653.1 |
| 5,800,352 A | 9/1998 | Ferre et al. | 600/407 |
| 5,803,089 A | 9/1998 | Ferre et al. | 128/897 |
| 5,810,728 A | 9/1998 | Kuhn | 600/410 |
| 5,829,444 A | 11/1998 | Ferre et al. | 128/897 |
| 5,831,260 A | 11/1998 | Hansen | 250/221 |
| 5,833,608 A | 11/1998 | Acker | 600/409 |
| 5,836,954 A | 11/1998 | Heilbrun et al. | 600/130 |
| 5,840,024 A | 11/1998 | Taniguchi et al. | 600/424 |
| 5,840,025 A | 11/1998 | Ben-Haim | 600/424 |
| 5,851,183 A | 12/1998 | Bucholz | 600/425 |
| 5,868,674 A | 2/1999 | Glowinski et al. | 600/410 |
| 5,871,445 A | 2/1999 | Bucholz | 600/407 |
| 5,873,822 A | 2/1999 | Ferre et al. | 600/407 |
| 5,891,034 A | 4/1999 | Bucholz | 600/426 |
| 5,913,820 A | 6/1999 | Bladen et al. | 600/407 |
| 5,920,395 A | 7/1999 | Schulz | 356/375 |
| 5,950,629 A | 9/1999 | Taylor et al. | 128/897 |
| 5,954,647 A | 9/1999 | Bova et al. | 600/407 |
| 5,967,980 A | 10/1999 | Ferre et al. | 600/424 |
| 5,976,156 A | 11/1999 | Taylor et al. | 606/130 |
| 5,987,349 A | 11/1999 | Schulz | 600/427 |
| 6,019,725 A | 2/2000 | Vesely et al. | 600/447 |
| 6,024,408 A | 2/2000 | Greenberg et al. | 600/102 |
| 6,073,043 A * | 6/2000 | Schneider | 600/424 |
| 6,104,944 A | 8/2000 | Martinelli | 600/424 |
| 6,122,538 A | 9/2000 | Sliwa, Jr. et al. | 600/407 |
| 6,161,032 A | 12/2000 | Acker | 600/424 |

* cited by examiner

COIL STRUCTURES AND METHODS FOR GENERATING MAGNETIC FIELDS

CROSS-REFERENCE TO RELATED APPLICATIONS

The following United States patent applications, which were concurrently filed with this one on Oct. 28, 1999, are fully incorporated herein by reference: Method and System for Navigating a Catheter Probe in the Presence of Field-influencing Objects, by Michael Martinelli, Paul Kessman and Brad Jascob, Ser. No. 60/161,991; Patient-shielding and Coil System, by Michael Martinelli, Paul Kessman and Brad Jascob, Ser. No. 60/161,989; Navigation Information Overlay onto Ultrasound Imagery, by Paul Kessman, Troy Holsing and Jason Trobaugh, Ser. No. 10/047,927; Registration of Human Anatomy Integrated for Electromagnetic Localization, by Mark W. Hunter and Paul Kessman, Ser. No. 09/429,569; System for Translation of Electromagnetic and Optical Localization Systems, by Mark W. Hunter and Paul Kessman, Ser. No. 09/429,568; Surgical Communication and Power System, by Mark W. Hunter, Paul Kessman and Brad Jascob, Ser. No. 09/428,722; and Surgical Sensor, by Mark W. Hunter, Sheri McCoid and Paul Kessman, Ser. No. 09/428,721.

This application claims the benefit of U.S. Provisional Application No. 60/161,990, filed Oct. 28, 1999, the contents of which are incorporated herein by reference in their entirety, and from which priority is claimed.

STATEMENT REGARDING FEDERALLY SPONSORED RESEARCH

Not Applicable

REFERENCE TO MICROFICHE APPENDIX

Not Applicable

BACKGROUND OF THE INVENTION

This invention relates to methods of and devices for generating magnetic fields, and more particularly to the physical characteristics of magnetic field generating coils.

There are various known methods for determining the position of a medical instrument during surgery. For instance, U.S. Pat. No. 5,592,939 to Martinelli, hereby incorporated by reference, discloses a method and apparatus for detecting the position of a medical instrument during surgery. This invention, however, is not limited to any specific method of determining the position of a medical instrument during surgery. For example, FIG. 1 is a diagram of an examination deck 200 with a medical instrument in a surgical environment. During surgery, for example, examination deck 200 lies below a patient. The medical device, such as a catheter 203, is placed inside the patient. Catheter 203 has a coil 14 at its distal end. Methods and systems consistent with the '939 patent determine the location and orientation of catheter 203 inside the patient relative to examination deck 200.

Catheter 203 includes a conductor 16 that leads along catheter 203 to a location outside the patient. Examination deck 200 comprises magnetic field generating coils that produce magnetic fields within a navigational domain 12. The magnetic fields induce voltage signals in sensing coil 14. Measurements taken at conductor 16 of the induced voltage signals provide sufficient information to compute the orientation and position of sensing coil 14.

FIGS. 2A, 2B, 2C, and 3 show magnetic field generating coils. FIG. 2A is a diagram of a coil set 202 for generating a substantially uniform magnetic field in the X direction. Driver 28 supplies current in the direction indicated by the arrows. Coil elements 20 and 22 are horizontal, while coil elements 24 and 26 are vertical. Elements 24 and 26 are "compensation" coils, i.e. "Cunard" coils, which cancel some undesirable field components generated by elements 20 and 22 in the Y and Z directions. As a result, coil set 202 generates a substantially uniform X direction field as indicated by field line 27.

FIG. 2B is a diagram of a coil set 204 for generating a substantially uniform magnetic field in the Y direction. Coil set 204 includes element 30 spaced from element 32, but parallel to element 32. Driver 34 supplies current in the direction indicated by the arrows. Coil set 204 generates a substantially uniform Y direction field as indicated by field line 33.

FIG. 2C is a diagram of a coil set 206 for generating a substantially uniform magnetic field in the Z direction. Driver 44 supplies current in the direction indicated by the arrows. Coil elements 36 and 38 are horizontal, while elements 40 and 42 are vertical. Elements 40 and 42 are compensation coils, i.e. Cunard coils, that cancel some undesirable field components in the X and Y directions. As a result, coil set 206 generates a substantially uniform Z direction magnetic field as indicated by field line 43.

FIG. 3 is a diagram of three pairs of delta coil sets 300 for generating three gradient magnetic fields. The configuration includes a first delta coil pair 50–52, a second delta coil pair 54–56, and a third delta coil pair 58–60. Delta coil pairs 50–52, 54–56, and 58–60 are arranged in a circular orientation about the Y axis such that there is an axis perpendicular to the direction of elongation of the coils at , 120 , and 240 relative to the Z axis. The magnetic field generated by long delta coil 50 and short delta coil 52 is shown by the field lines extending from coils 50–52. The field lines from delta coils 50–52 group form a family of substantially constant signal surfaces, i.e. the magnetic fields have a spatial gradient in two of the axis dimensions and a substantially zero field value in the remaining axial dimension.

Discussion of FIGS. 1, 2A, 2B, 2C, and 3 are for illustrative purposes only. See U.S. Pat. No. 5,592,939 for further examples.

FIG. 3B is a diagram of a patient undergoing cranial surgery with a device consistent with this invention. In FIG. 3B, the medical device is a probe 302 that is placed inside a head 308 of a patient.

Coil sets 202–204, 300 in FIGS. 2A–2C, and 3 are contained within the examination deck 200 of FIG. 1. Placing all these coils in examination deck 200, however, causes examination deck 200 to be relatively thick. It is desirable, however, that examination deck 200 be relatively thin for a number of reasons. First, a thinner examination deck 200 is lighter, less cumbersome, and requires less space in a crowded surgery room. Second, if coil sets 202–204, 300 are arranged so that each is a different distance from navigational domain 12, then the magnetic field strength in navigational domain 12 from each coil set is different. Different magnetic field strengths reduce accuracy of the positioning system. Further, it can be less expensive and easier to manufacturer a thin examination deck as compared to a thick examination deck.

Examination deck 200, in turn, is placed on an examination table 306. FIG. 3A is a diagram of examination deck 200 placed on the examination fable 306, consistent with this invention, in a medical setting. Examination table 306 introduces other design constraints,including the width and length of the examination deck 200, which introduces design constrains on the size and shape of coils inside examination deck 200. Preferably, the magnetic field generating coils are such that examination deck easily fits onto standard size examination tables, such as examination table 306.

Therefore, it is desirable to provide an apparatus that allows coil sets to be arranged substantially coplanar with respect to navigational domain 12. It is also desirable to provide an apparatus that allows examination deck 200 to fit on a standard examination table.

It is an object of the present invention to substantially overcome the above-identified disadvantages and drawbacks of the prior art.

SUMMARY OF THE INVENTION

The foregoing and other objects are achieved by the invention which in one aspect comprises an apparatus for determining a location of a sensor in a surgical navigation domain. The apparatus includes a first magnetic field generator having a first coil set, a second magnetic field generator having a second coil set. The first and second coil sets are disposed substantially within a common plane. The apparatus further includes a processor configured to receive a plurality of signals. The processor calculates the location of the sensor from the plurality of signals. The sensor produces the plurality of signals in response to magnetic fields generated by the first and second magnetic field generators.

In another embodiment of the invention, the first coil set includes at least one delta coil pair for generating a gradient magnetic field-in the navigation domain.

In another embodiment of the invention, each delta coil pair further includes one or more end correction coils. Each delta coil pair is electrically coupled to the corresponding end correction coil, and current flows through the end correction coil in a direction opposite of the direction of the current flowing through the corresponding delta coil pair.

In another embodiment of the invention, the second coil set includes at least one uniform coil pair for generating a uniform magnetic field in the navigational domain.

In another embodiment of the invention, the first coil set includes a first delta coil pair longitudinally oriented along a first axis, a second delta coil pair longitudinally oriented along a second axis, and a third delta coil pair longitudinally oriented along a third axis. The three delta coil pairs are arranged such that the second axis is rotated within the common plane substantially sixty degrees with respect to the first axis, and the third axis is rotated within the common plane substantially one hundred and twenty degrees with respect to the first axis.

In another embodiment of the invention, each of the first, second arid third delta coil pairs lies within a distinct plane that is parallel to the common plane, such that the delta coil pairs overlap one another.

In another embodiment of the invention, each of the first, second and third delta coil pairs includes two or more distinct coil elements, electrically coupled, such that the aggregate of the distinct coil elements produces the corresponding gradient magnetic field.

In another embodiment of the invention, intersecting delta coil pairs share one or more common coil elements.

In another embodiment of the invention, intersecting delta coil pairs include distinct coil elements in an intersecting region where the delta coil pairs overlap.

In another embodiment of the invention, each of the delta coil pairs further include one or more end correction coils. Each of the delta coil pairs is electrically coupled to the corresponding end correction coil, and electrical current flows through the end correction coils in a direction opposite of the direction of the current flowing through the corresponding delta coil pair.

In another embodiment of the invention, at least one of the delta coil pairs is characterized by a length that is different from the length of the other delta coil pairs.

In another embodiment of the invention, each of the delta coil-pairs includes a short coil and a long coil. The short coil further includes a first end correction element and a second end correction element for reducing unwanted magnetic field components. Electrical current flows through the end correction coils in a direction opposite of the direction of the current flowing through the corresponding short coil. The long coil further includes a central compensating coil for reducing unwanted magnetic field components. Electrical current flows through the central compensating coil in a direction opposite of the direction of the current flowing through the corresponding long coil.

In another embodiment of the invention, one or more of the delta coil pairs overlap a coplanar uniform coil pair.

In another embodiment of the invention, each of the one or more overlapping delta coil pairs includes two or more distinct coil elements. The distinct coil elements are electrically coupled, such that the aggregate of the distinct coil elements produces the corresponding gradient magnetic field.

In another aspect, the invention comprises an apparatus for determining a location of a sensor in a surgical navigation domain. The apparatus includes a first magnetic field generator including at least one delta coil pair for generating a gradient magnetic field in said navigation domain. The at least one delta coil pair disposed within a first plane. The apparatus further includes a second magnetic field generator including at least one uniform coil pair for generating a uniform magnetic field in the navigational domain. The at least one uniform coil pair disposed within a second plane. The first plane is offset from the second plane by an offset angle calculated to reduce undesirable uniform field components. The apparatus also includes a processor, configured to receive a plurality of signals, for calculating the location of the sensor from the plurality of signals. The sensor produces the plurality of signals in response to magnetic, fields generated by the first and second magnetic field generators.

In another aspect, the invention comprises an apparatus for determining a location of a sensor in a surgical navigation domain, including a first magnetic field generator having a common coil, a second magnetic field generator also including the common coil, and a processor for calculating the location of the sensor. The sensor produces a plurality of signals in response to a first magnetic field generated by the first magnetic field generator, and in response to a second magnetic field of a different shape, with respect to the first magnetic field generated by the second magnetic field generator.

In yet another aspect, the invention comprises a method of determining a location of a sensor in a surgical navigation domain. The method includes generating a first magnetic field using a first magnetic field generator having a first coil set, and generating a second magnetic field using a second magnetic field generator having a second coil set. The first and second coils are disposed substantially within a common plane. The method further includes calculating the location of the sensor from a plurality of signals. The sensor produces the plurality of signals in response to magnetic fields generated by the first and second generated magnetic fields.

In another embodiment, the method further includes generating a gradient magnetic field in said navigation domain using at least one delta coil pair for generating.

In another embodiment, the method further includes generating a gradient magnetic field in said navigation domain using two or more distinct coil elements, electrically coupled, such that the aggregate of the distinct coil elements produces the corresponding gradient magnetic field.

In another embodiment, the method further includes generating a gradient magnetic field in said navigation domain using delta coil pairs having one or more end correction coils. Each of the delta coil pairs is electrically coupled to the corresponding end correction coil, and electrical current flows through the end correction coils in a direction opposite of the direction of the current flowing through the corresponding delta coil pair.

In another aspect, the invention comprises a method of determining a location of a sensor in a surgical navigation domain, including generating a gradient magnetic field in said navigation domain using a first magnetic field generator including at least one delta coil pair disposed within a first plane. The method further includes generating a uniform magnetic field in the navigational domain using a second magnetic field generator including at least one uniform coil pair. The at least one uniform coil pair is disposed within a second plane. The first plane is offset from the second plane by an offset angle calculated to reduce undesirable uniform field components. The method also includes calculating the location of the sensor from a plurality of signals. The sensor produces the plurality of signals in response to magnetic fields generated by the first and second generated magnetic field.

In another aspect, the invention comprises a method of determining a location of a sensor in a surgical navigation domain, including generating a first magnetic field using a magnetic field generator that includes a common coil. The method further includes generating a second magnetic field of a different shape than the first magnetic field, using a second magnetic field generator that includes the common coil. The method also includes calculating the location of the sensor from a plurality of signals. The sensor produces the plurality of signals in response to magnetic fields generated by the first and second magnetic field generators.

BRIEF DESCRIPTION OF DRAWINGS

The foregoing and other objects of this invention, the various features thereof, as well as the invention itself, may be more fully understood from the following description, when read together with the accompanying drawings in which.

DESCRIPTION OF THE PREFERRED EMBODIMENTS

The following description of embodiments of this invention refers to the accompanying drawings. Where appropriate, the same reference numbers in different drawings refer to the same or similar elements.

Figure 1:
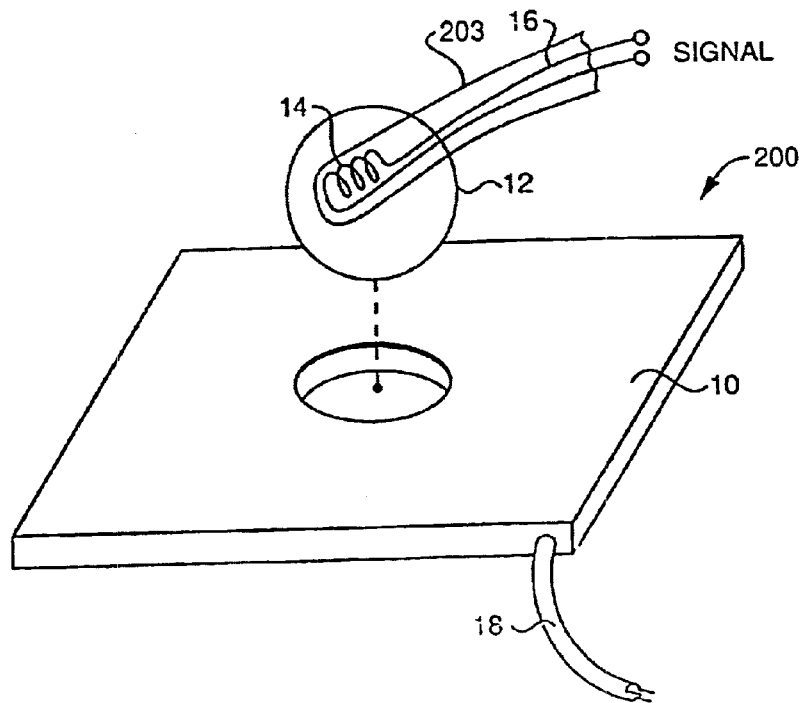
FIG. 1 is a diagram of an examination deck 200 with a medical instrument in a medical environment.
Figure 2A:
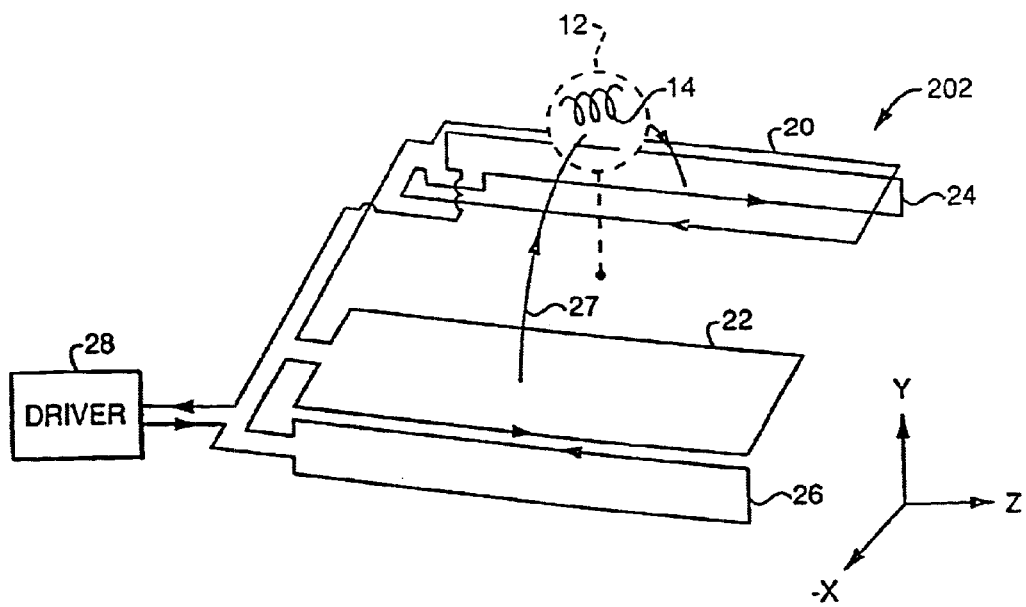
FIGS. 2A, 2B, 2C, and 3 show magnetic field generating coils.
Figure 2B:
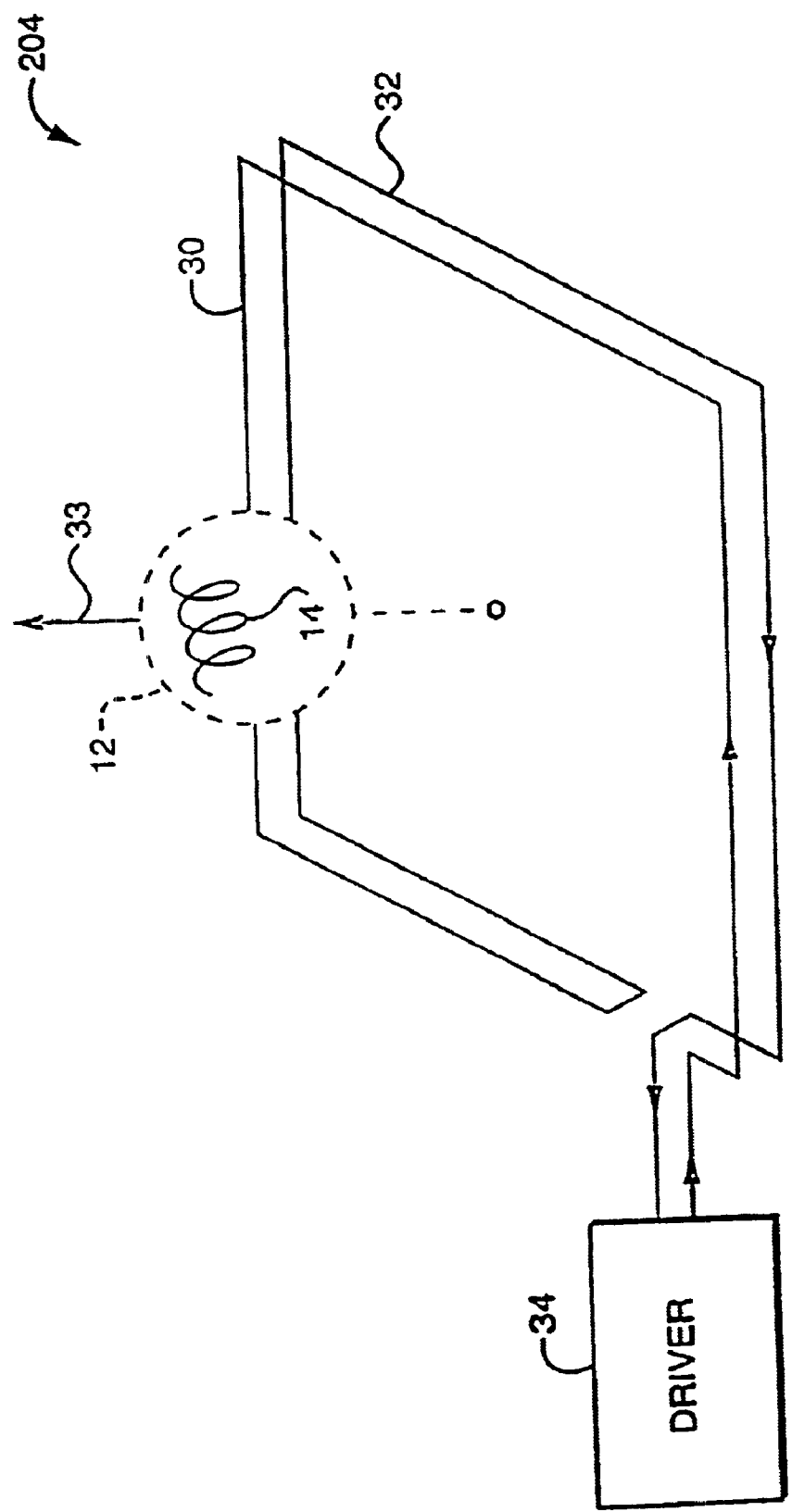
Figure 2C:
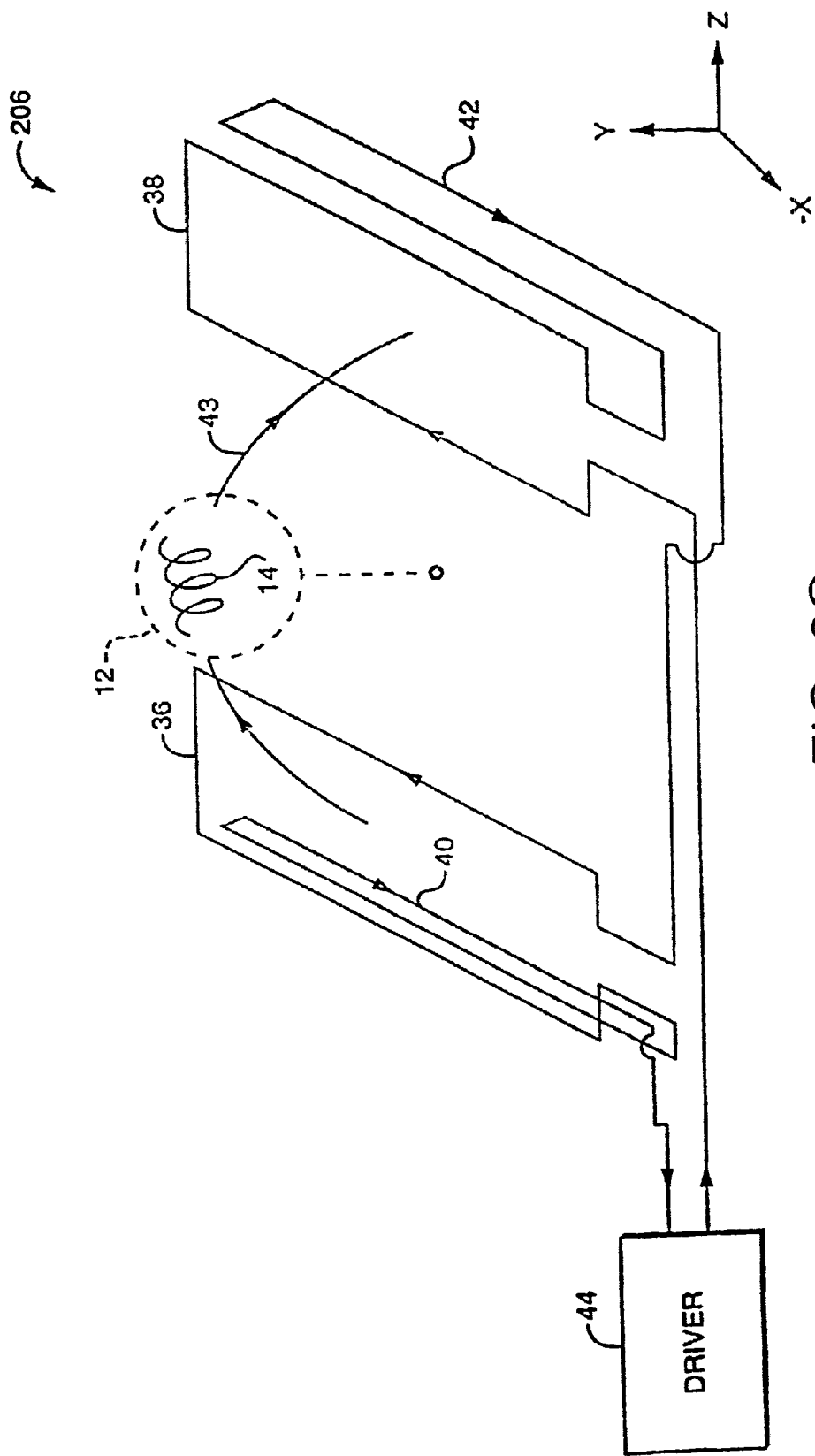
Figure 3:
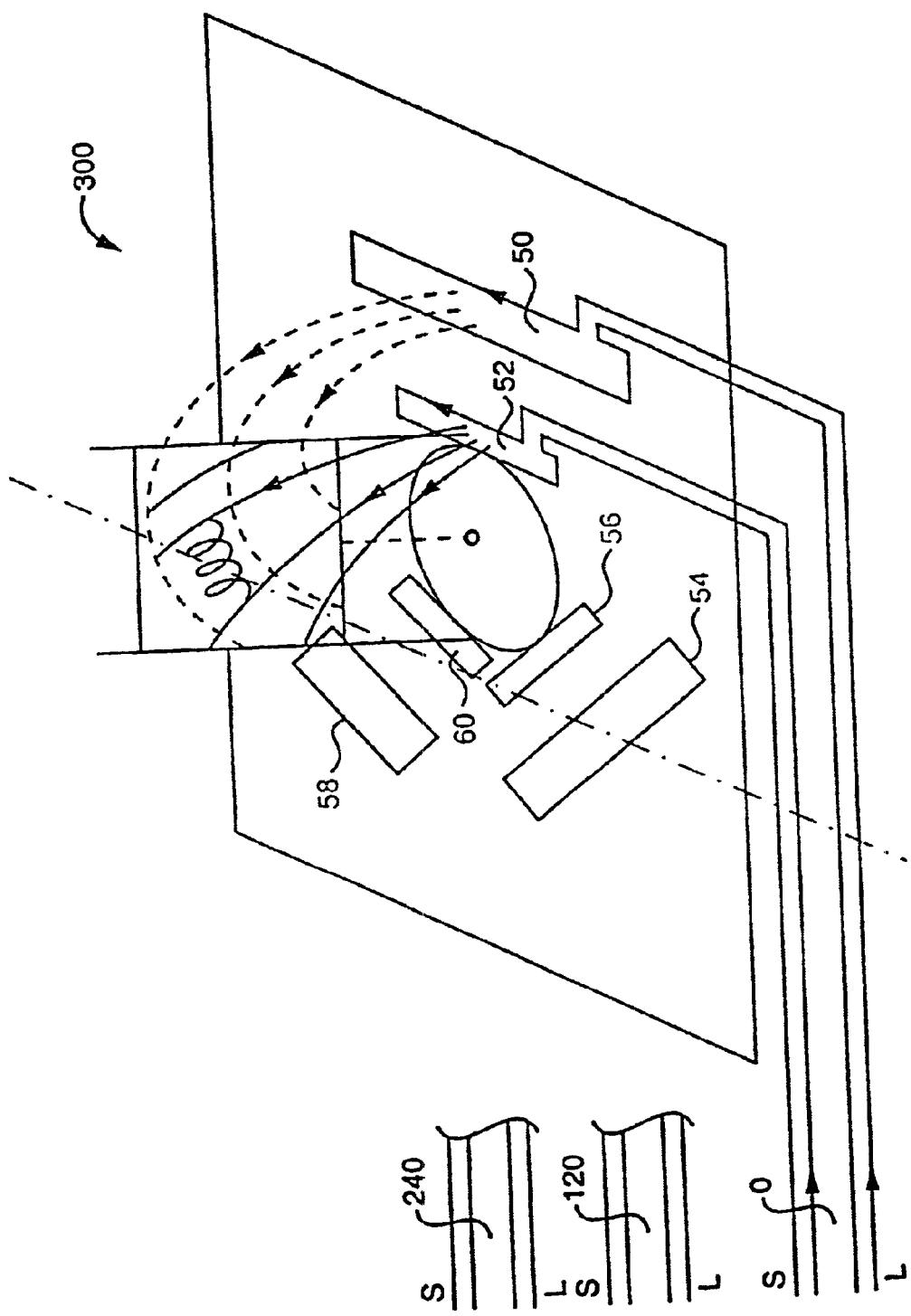
Figure 3A:
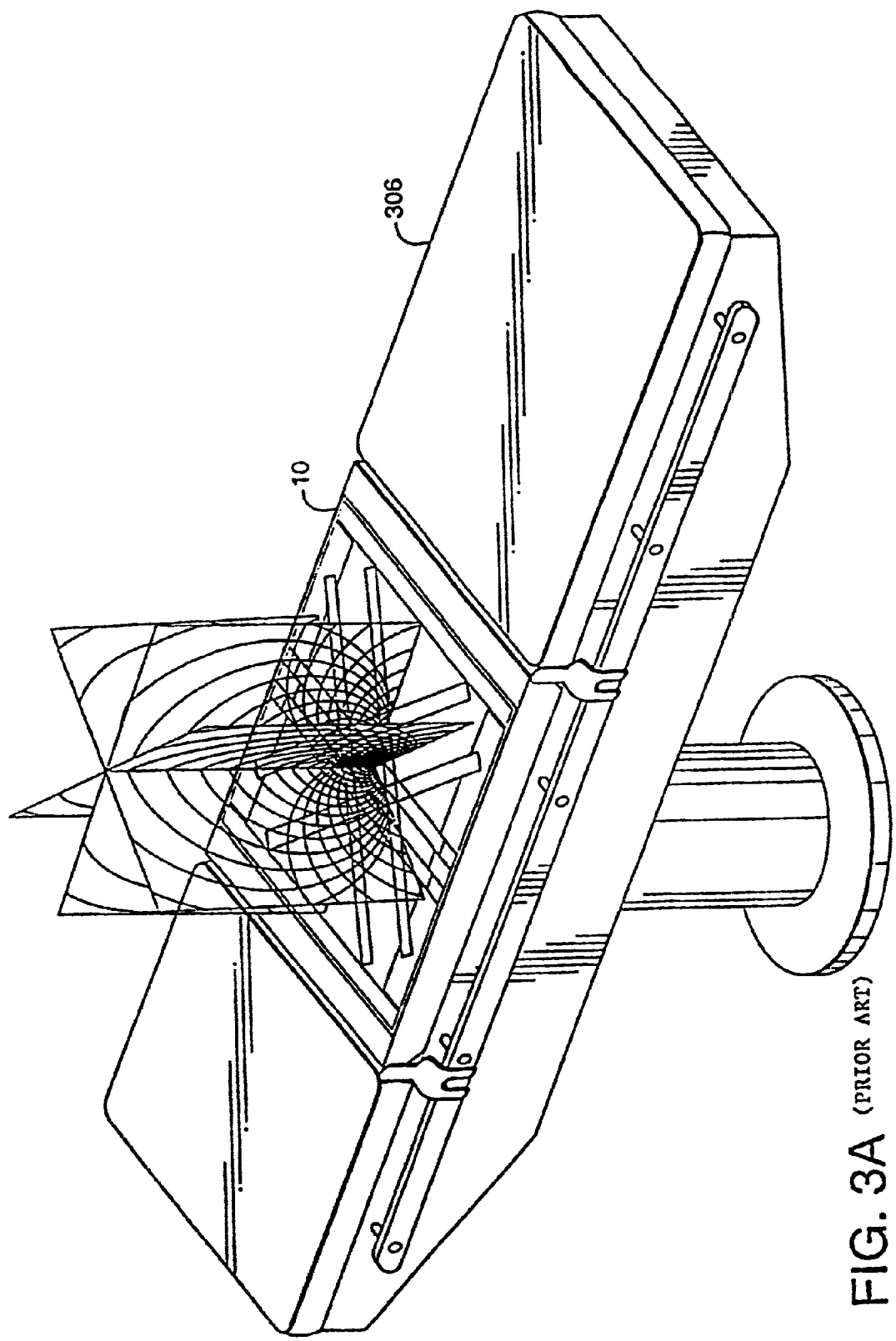
FIG. 3A is a diagram of the examination deck in FIG. 1 placed on an examination table, consistent with this invention, in a medical setting.
Figure 3B:
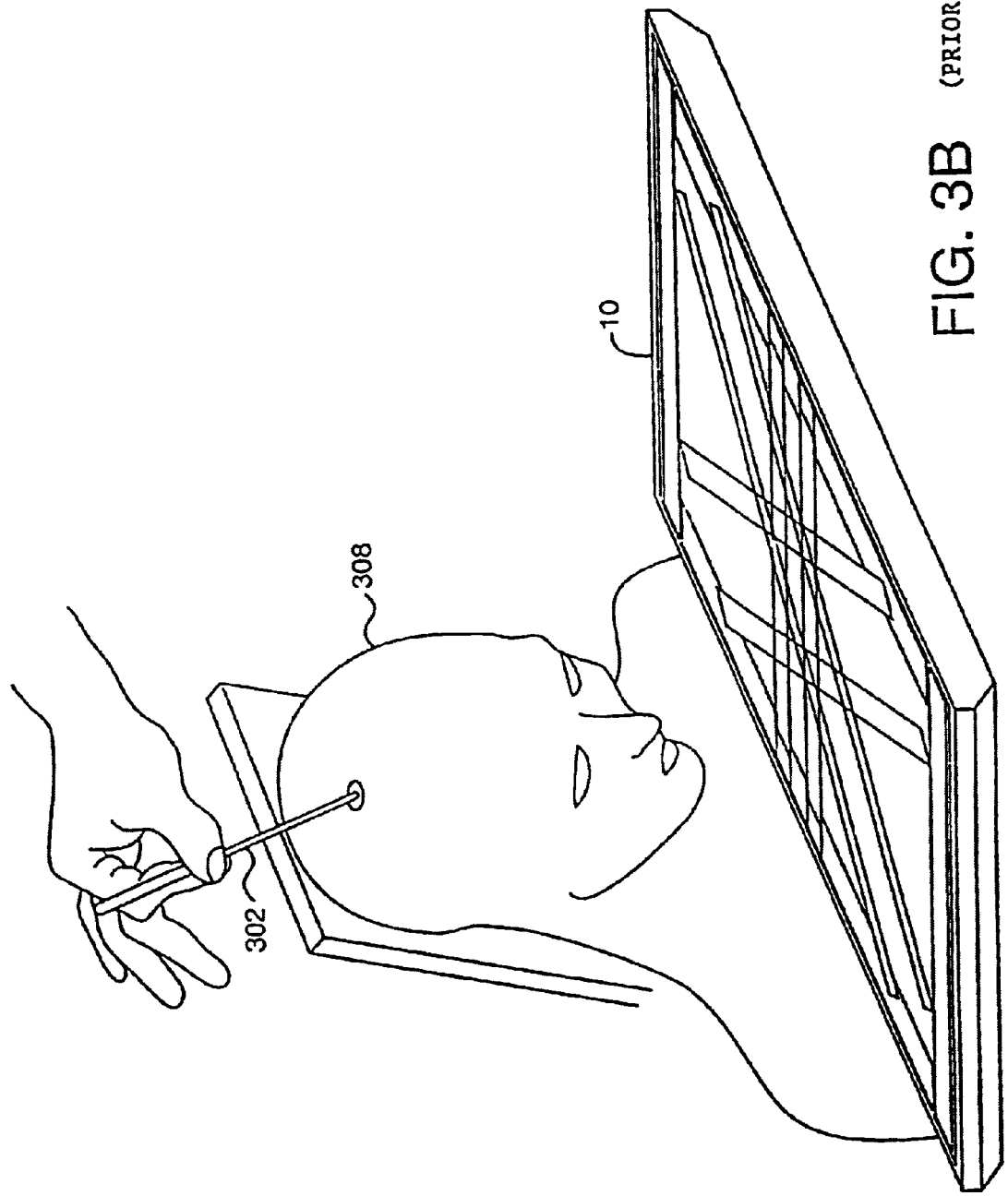
FIG. 3B is a diagram of a patient undergoing cranial surgery with a device consistent with this invention.
Figure 4:
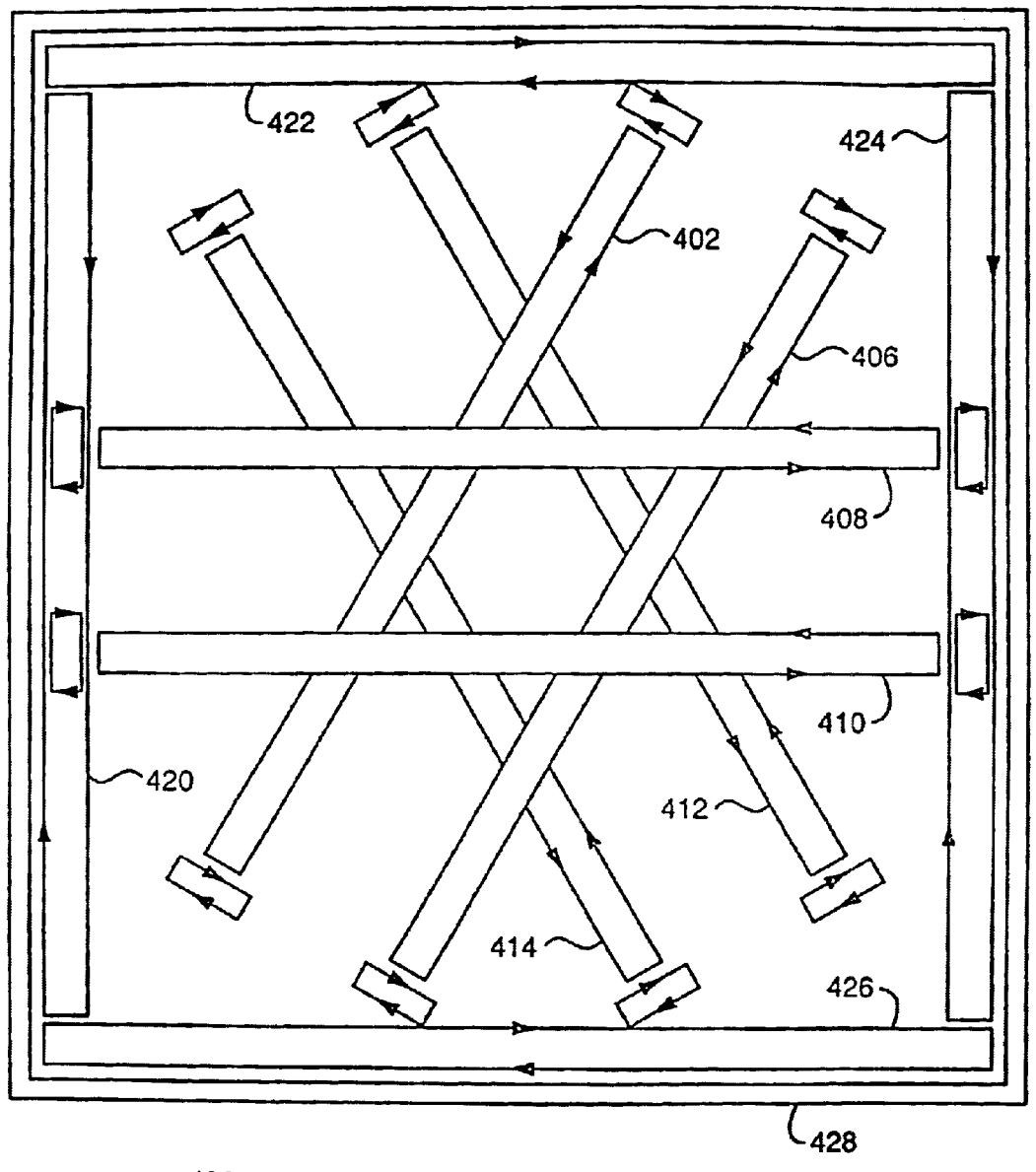
FIG. 4 is a top view of coil sets arranged to be disposed within in examination deck 200.

FIG. 4 is a top view of coil sets, consistent with this invention, arranged to be placed in examination deck 200. An arrangement 400 comprises a first delta coil pair 402–406, a second delta coil pair 408–410, and a third delta coil pair 412–414. First through third delta coil pairs 402–414 create gradient fields similar to those described with respect to FIG. 3 above. Arrangement 400 also comprises a first uniform coil pair 420, 424, and a second uniform coil pair 426, 422. First and second uniform coil pairs generate substantially uniform magnetic fields similar to the fields described with respect to FIGS. 2A and 2C above. Arrangement 400 also comprises a girth coil 428 that creates a substantially uniform magnetic field similar to the magnetic field described with respect to FIG. 2B above. Arrows indicate a possible direction of current flowing in the coils. Arrangement 400 is advantageous because it may be configured to in examination deck 200 so that it can fit on and be integrated into a standard examination or surgical table.

Figure 5:
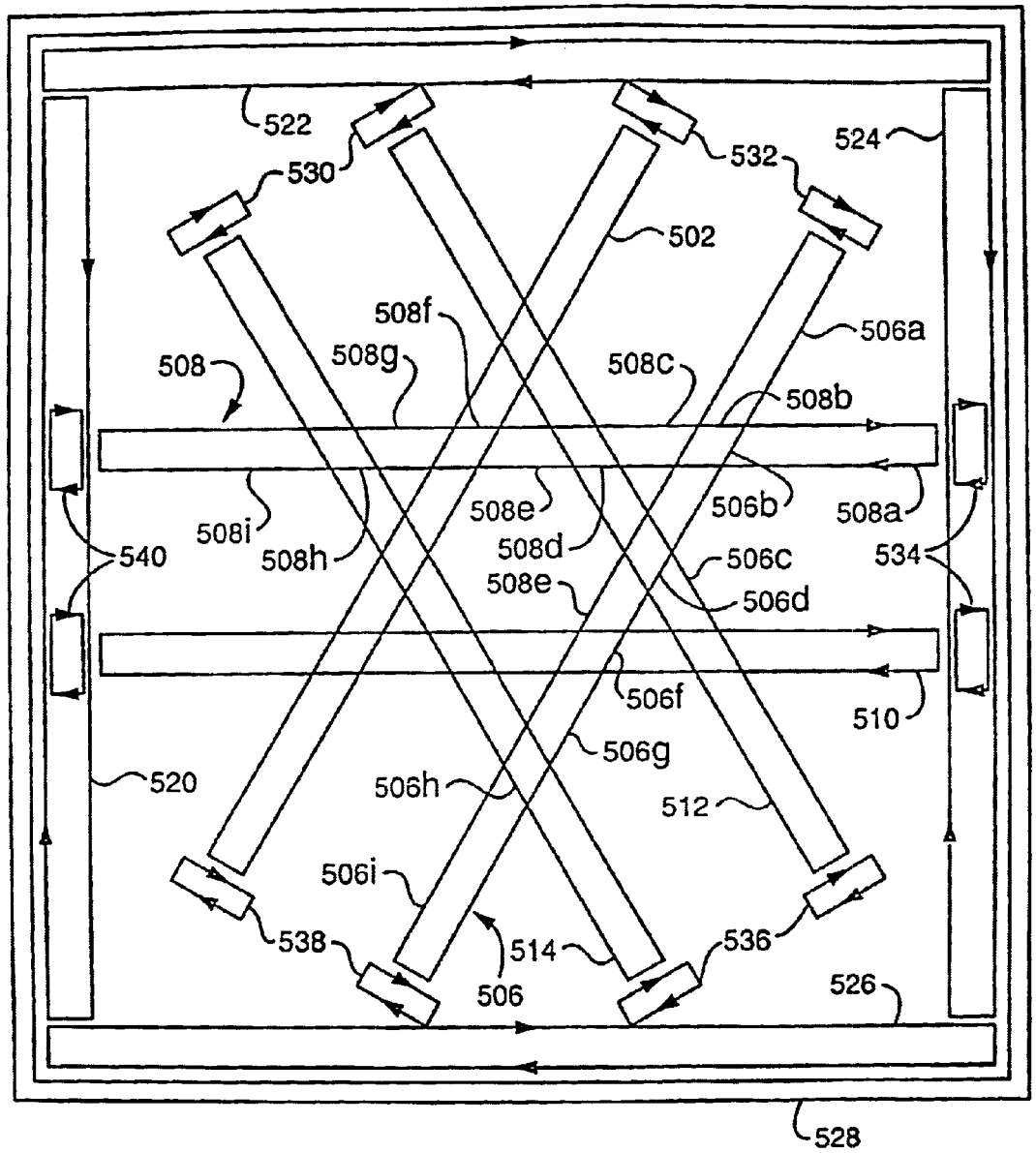
FIG. 5 is a top view of coil sets, consistent with this invention, arranged substantially coplanar for generating magnetic fields.

Methods and systems consistent with this invention arrange the coil sets so that they are substantially coplanar. FIG. 5 is a top view of coil sets, consistent with this invention, arranged substantially coplanar for generating magnetic fields. An arrangement 500 comprises a first delta coil pair 502–506, a second delta coil pair 508–510, and a third delta coil pair 512–514. First through third delta coil pairs 508–514 create gradient fields similar to those described with respect to FIG. 3 above. Arrangement, 500 also comprises a first uniform coil pair 520, 524, and a second uniform coil pair 526, 522. First and second uniform coil pairs generate uniform magnetic fields similar to the fields described with respect to FIGS. 2A and 2C above. Arrangement 500 also comprises a girth coil 528 that creates a substantially uniform magnetic field similar to the magnetic field described with respect to FIG. 2B above. Arrows indicate a possible direction of current flowing in the coils.

In FIG. 5, coil 506 has nine elements 506a–i. When coil 506 generates a magnetic field, nine elements 506a–I are electrically connected in series so such that they produce magnetic fields that are nearly identical to coil 406 in FIG. 4. Coil 508 also has nine separate elements 508a–i. When coil 508 generates a magnetic field, nine elements 508a–I are electrically connected in series such that they produce magnetic fields that are nearly identical to coil 408 in FIG. 4. Coils 510, 512, 514, and 502 also comprise nine elements and are configured in a similar fashion.

Figure 6:
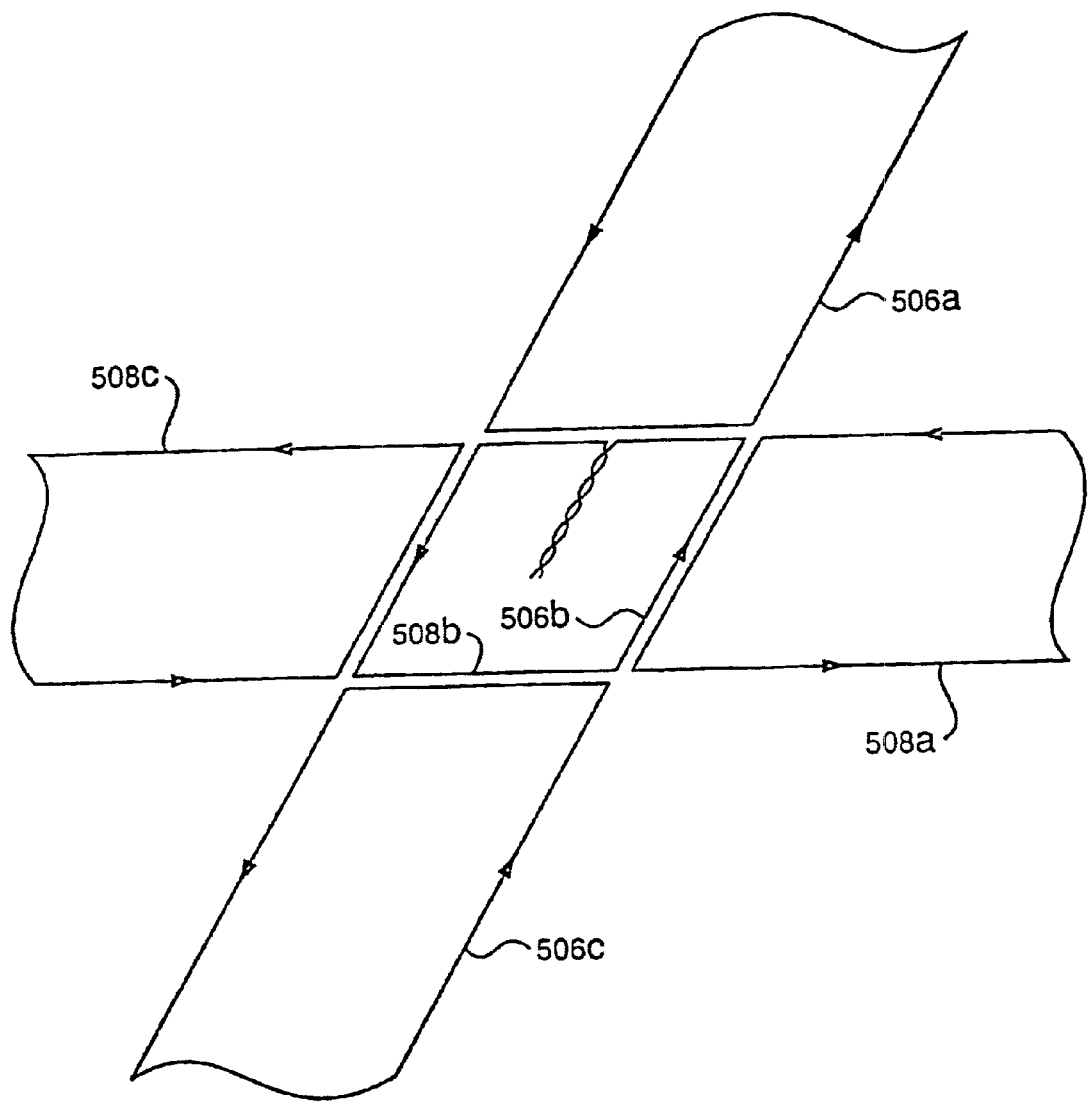
FIG. 6 is an exploded top view of a portion of two delta coils in FIG. 5, consistent with this invention, arranged substantially coplanar.

FIG. 6 is an exploded top view of a portion of two delta coils, consistent with this invention, arranged substantially coplanar. In the embodiment shown in FIG. 6, element 506b and element 508b are the same element. When coil 508 generates a magnetic field, switches 602, 604 create one electrical path through elements 508a, 508b (506b), and 508c. When coil 506 generates a magnetic field, switches 602, 604 create one electrical path through elements 506a, 506b (508b), and 508c. Arrows indicate a possible direction of current flowing in coils 506a–c and 508a–c. In this fashion, coil 508 and coil 506 share an element so that the coils can be arranged substantially coplanar.

Figure 6A:
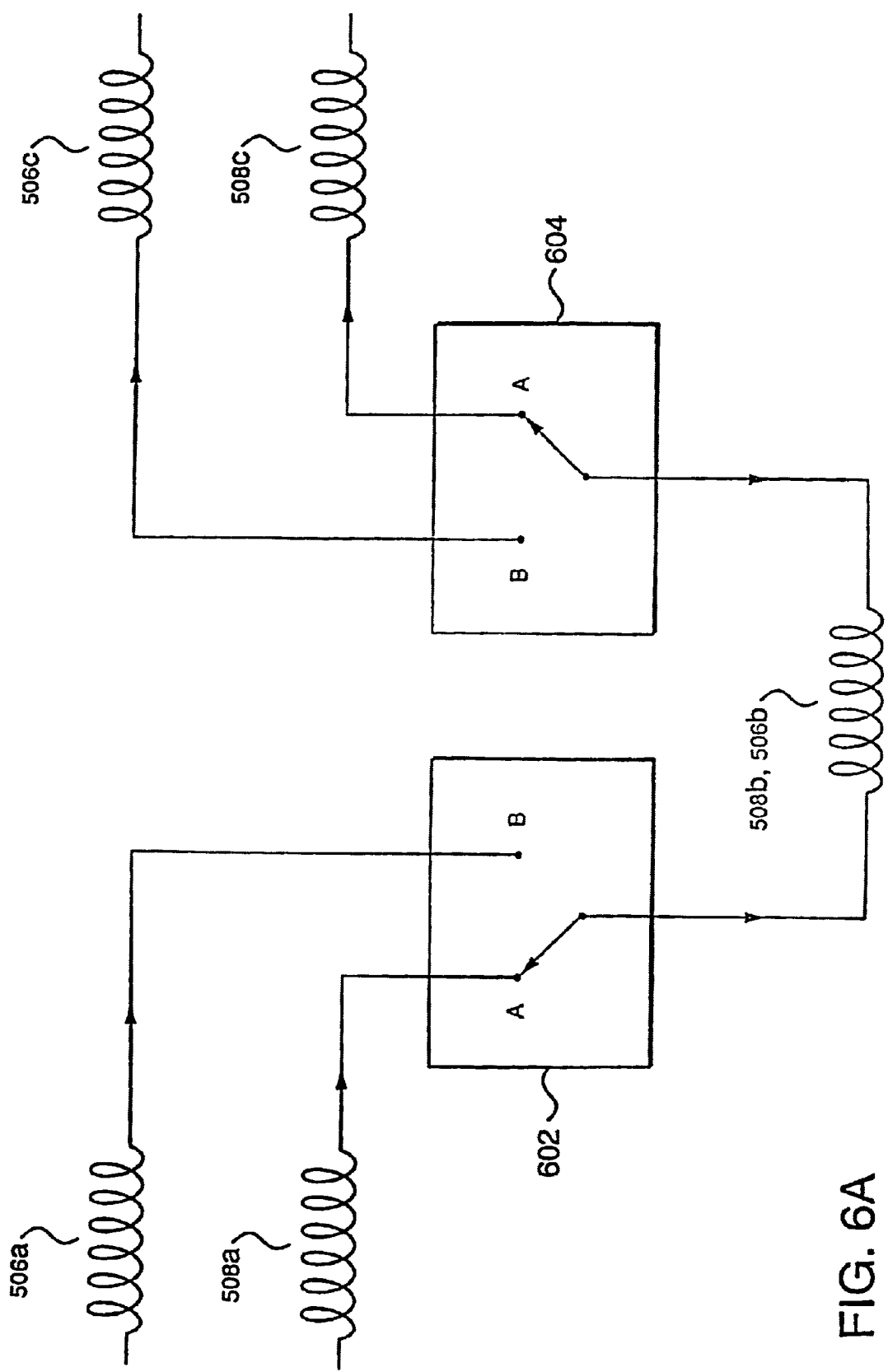
FIG. 6A is an electrical diagram of the coils shown in FIG. 6 configured with switches.

FIG. 6A is an electrical diagram of coils 506a–c and 508a–c shown in FIG. 6 configured with switches. When coil 508 generates a magnetic field, switches 602, 604 are in position A, which creates one electrical path through elements 508a, 508b (506b), and 508c. When coil 506 generates a magnetic field, switches 602, 604 are in position B, which creates one electrical path through elements 506a, 506b (508b), and 506c. Arrows indicate a possible direction of current flowing in coils 506a–c and 508a–c.

Figure 7:
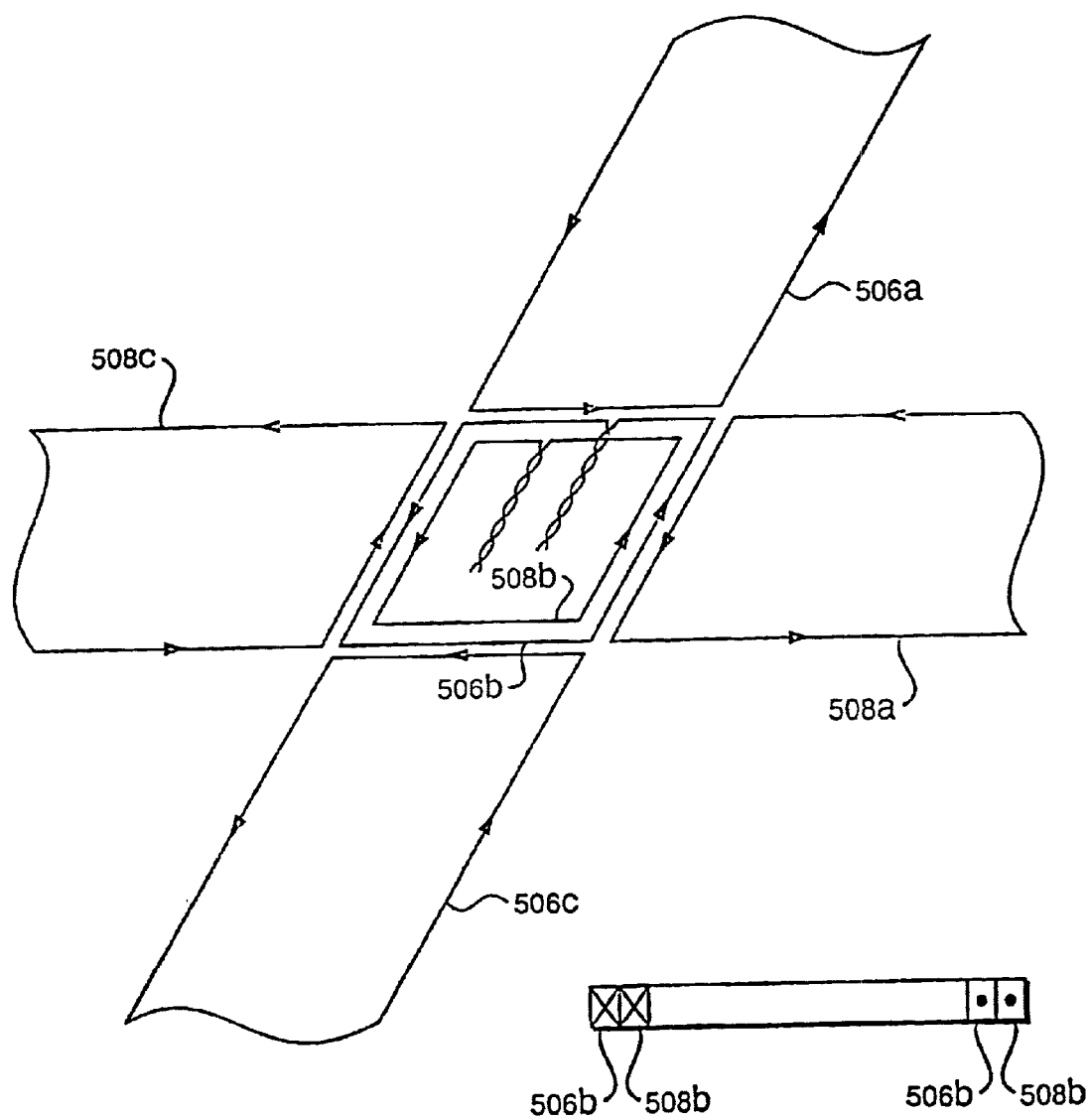
FIG. 7 is an exploded top view of a portion of two delta coils in FIG. 5, consistent with this invention, arranged substantially coplanar for generating magnetic fields.

FIG. 7 is an exploded top view of a portion of two delta coils, consistent with this invention, arranged substantially coplanar for generating magnetic fields. In the embodiment shown in FIG. 7, element 506b and element 508b are separate elements comprising two separate coils wrapped around substantially the same area. In the embodiment shown in FIG. 7, no switches are necessary, which eliminates complexity and hardware. Instead, elements 508a, 508b, and 508c, are always connected in series to form one electrical path. Likewise, elements 506a, 506b, and 506c are always connected in series to form one electrical path. FIG. 7 also provides a cross sectional view of elements 506b and 508b. As shown in this cross sectional view, coil 506b is wound outside coil 508b such that coil 506b encloses a greater area than coil 508b. In order to compensate for the smaller area enclosed by 508b, it is possible to include one or more extra windings of element 508b compared to element 506b.

Figure 7A:
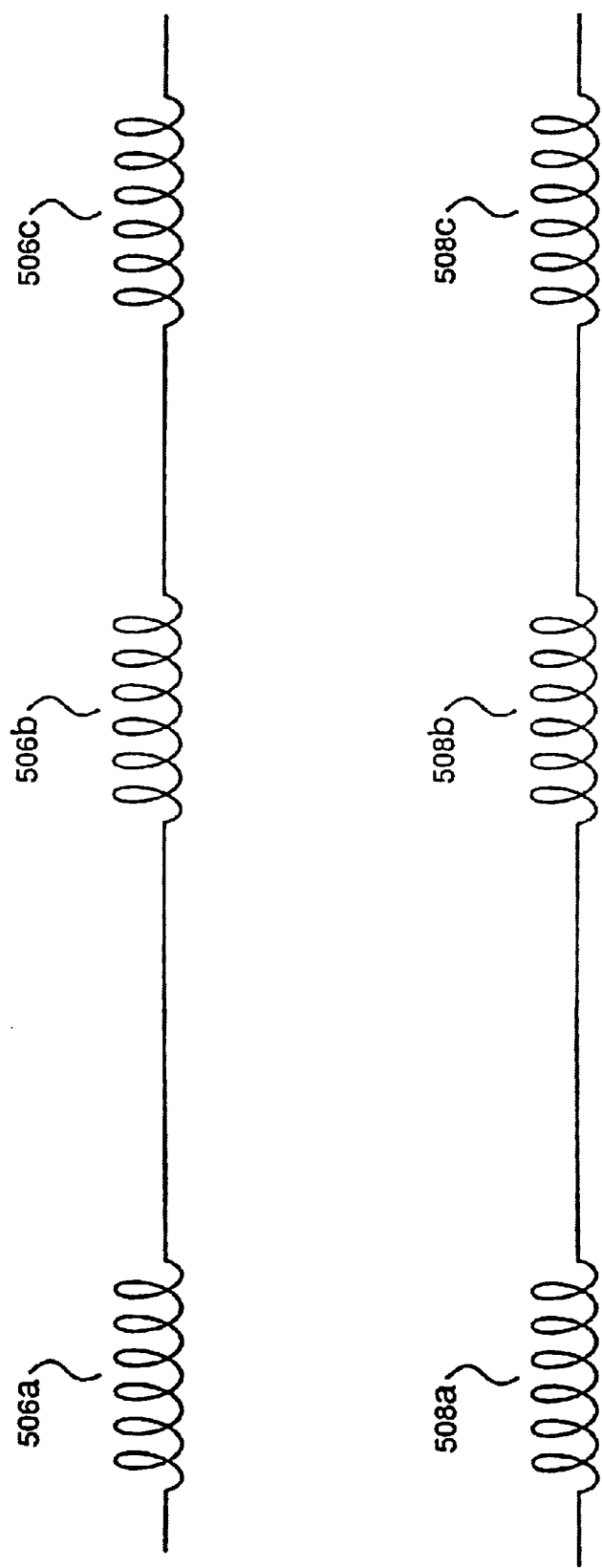
FIG. 7A is an electrical diagram of the coils shown in FIG. 7.

FIG. 7A is an electrical diagram of coils 506a–c and 508a–c of FIG. 7. In this embodiment, there are no switches and there is one-electrical path through elements 508a, 508b, and 508c. Likewise, there is one electrical path through elements 506a, 506b, and 506c. Arrows indicate a possible direction of current flowing in coils 506a–c and 508a–c.

Thus, referring back to FIG. 5, delta coil pairs 502–506, 508–510, and 512–514 lie substantially coplanar because of the configurations in FIGS. 6 and 7. In FIG. 5, there are twelve elements that "intersect," i.e., they may implement the configuration in FIGS. 6 and 7. Further, first uniform coil pair 520, 524 and second uniform coil pair 522, 526 are coplanar with first through third delta coil pairs 502–514. Lastly, girth coil 526 is coplanar with first through third delta coil pairs 502–514 and first unidirectional coil pair 520, 524 and second unidirectional coil pair 522, 528. Thus, all coil sets in FIG. 5 are coplanar.

FIG. 5 also shows "end correction" coils 530–540. Coils 530–540 are electrically in series with the nearest delta coil pairs, but carry current in the reverse direction. End correction coils 530–540 help to reduce unwanted magnetic field components in the non-gradient direction.

Figure 8:
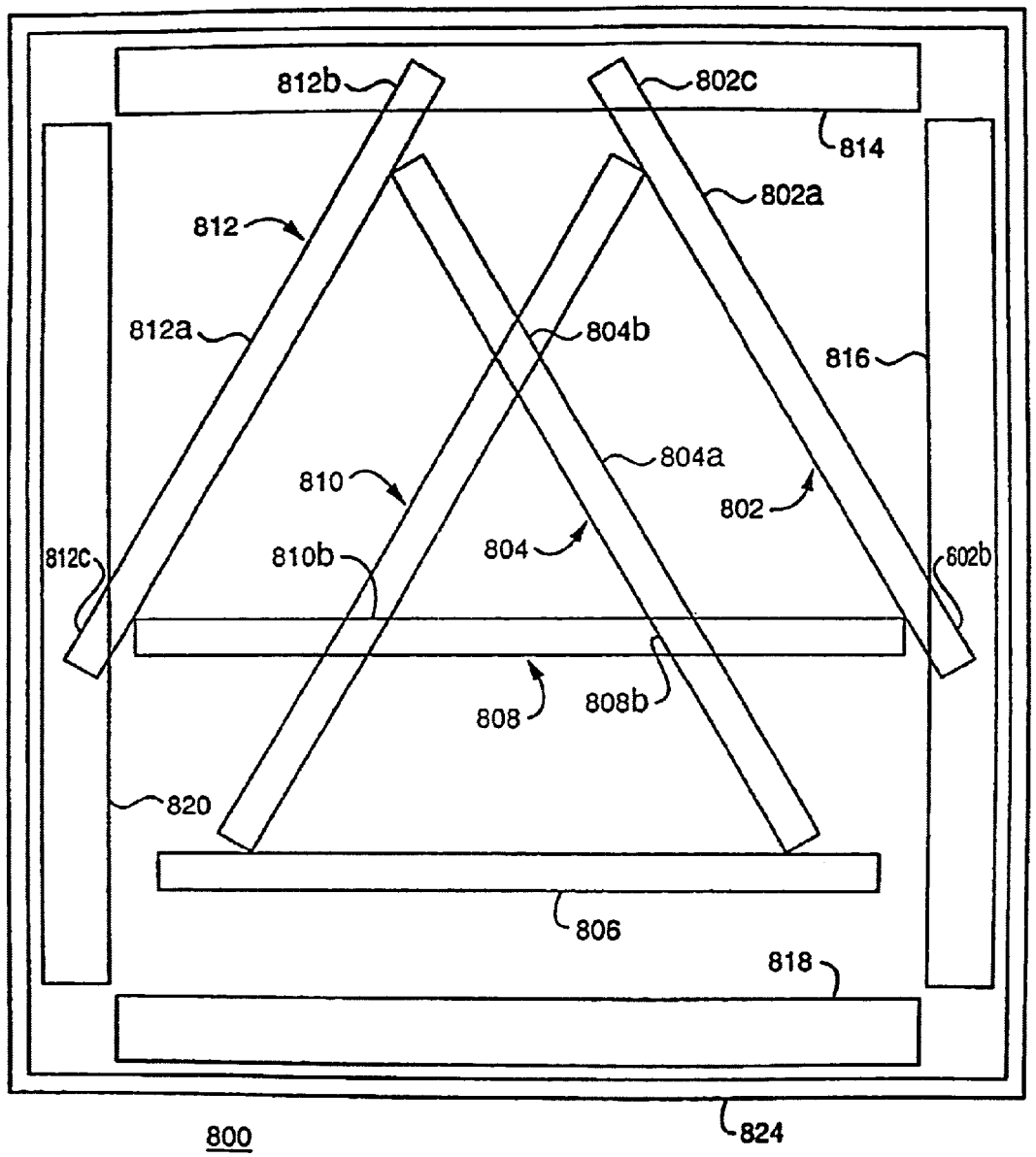
FIG. 8 is a top view of coil sets, consistent with this invention, arranged substantially coplanar for generating magnetic fields.
Figure 8A:
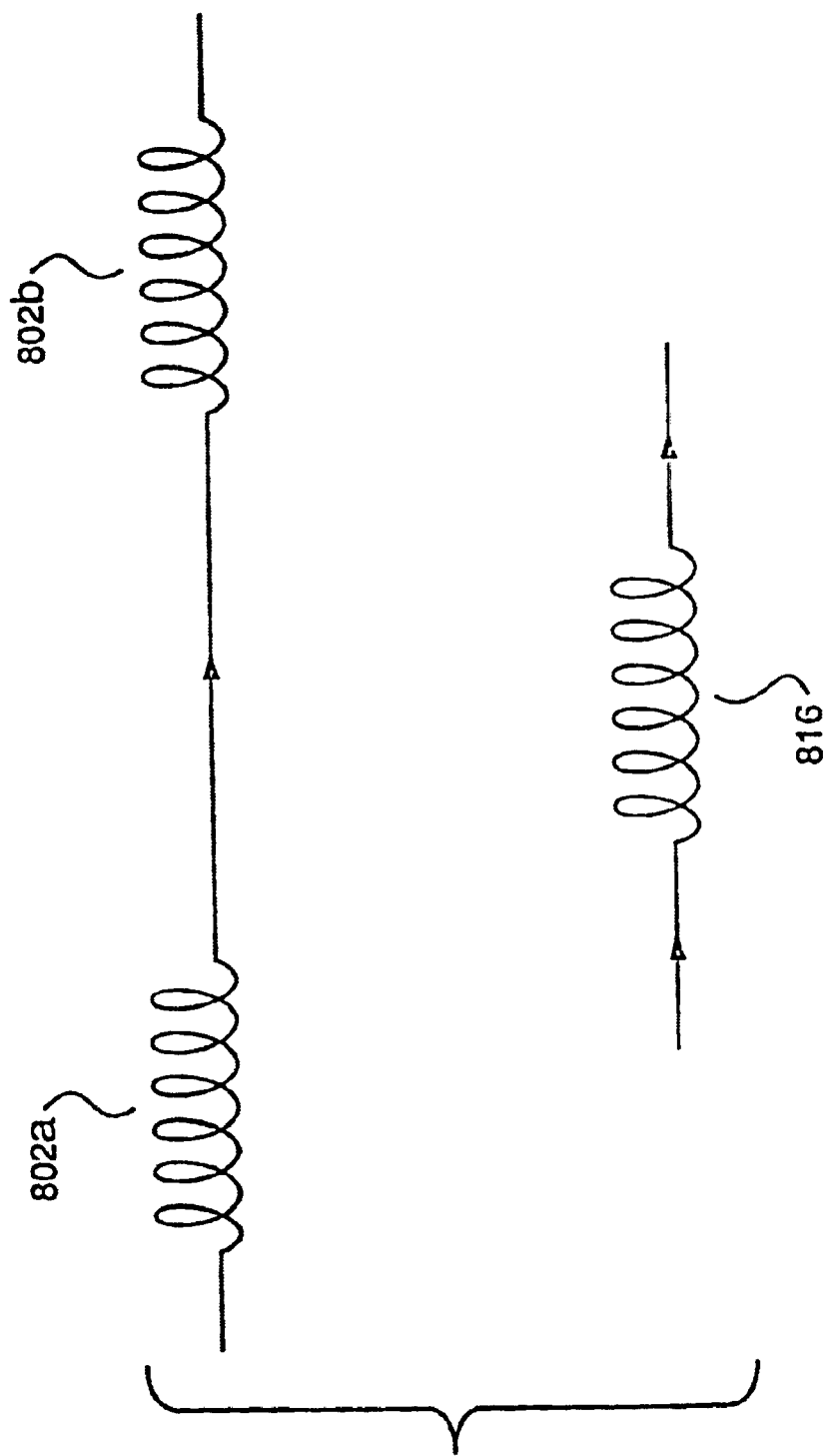
FIG. 8A is an electrical diagram of the coils shown in FIG. 9.

FIG. 8 is a top view of coil sets, consistent with this invention, arranged substantially coplanar for generating magnetic fields. The arrangement 800 comprises a first delta coil pair 802–804, a second delta coil pair 806–808, and a third delta coil pair 810–812. First through third delta coil pairs 802–812 create gradient fields similar to those described above with respect to FIG. 3. Arrangement 800 also comprises a first uniform coil pair 814, 818 and a second uniform coil pair 816, 820. First and second uniform coil pairs 816, 820 generate uniform magnetic fields similar to the magnetic fields discussed with respect to FIGS. 2A and 2C above. Arrangement 800 also comprises a girth coil 824 that generates a substantially uniform magnetic field similar to the magnetic fields discussed with respect to FIG. 2B above.

Also in FIG. 8, first delta coil set 802–804 intersects first uniform coil pair 814, 818 at element 802b. First delta coil set 802–804 also intersects second uniform coil pair 820, 816 at element 802c. Likewise, third delta coil set 810–812 intersects first uniform coil pair 814 at element 812b. Third coil set 810–812 also intersects second uniform coil pair 820, 816 at element 812c. Despite these intersections, a however, first and third delta coil set 802–804, 810–812 are arranged coplanar with first and second uniform coil set 814, 818, and 816, 820.

Also in FIG. 8, first delta coil set 802–804 intersects first uniform coil pair 814, 818 at element 802b. First delta coil set 802–804 also intersects second uniform coil pair 820, 816 at element 802c. Likewise, second delta coil set 810–812 intersects first uniform coil pair 814 at element 812b. Second delta coil set 810–812 also intersects second uniform coil pair 820, 816 at element 812c. Despite these intersections, however, first and second delta coil set 802–804, 810–812 are arranged coplanar with first and second uniform coil set 814, 818, and 816, 820.

Figure 9:
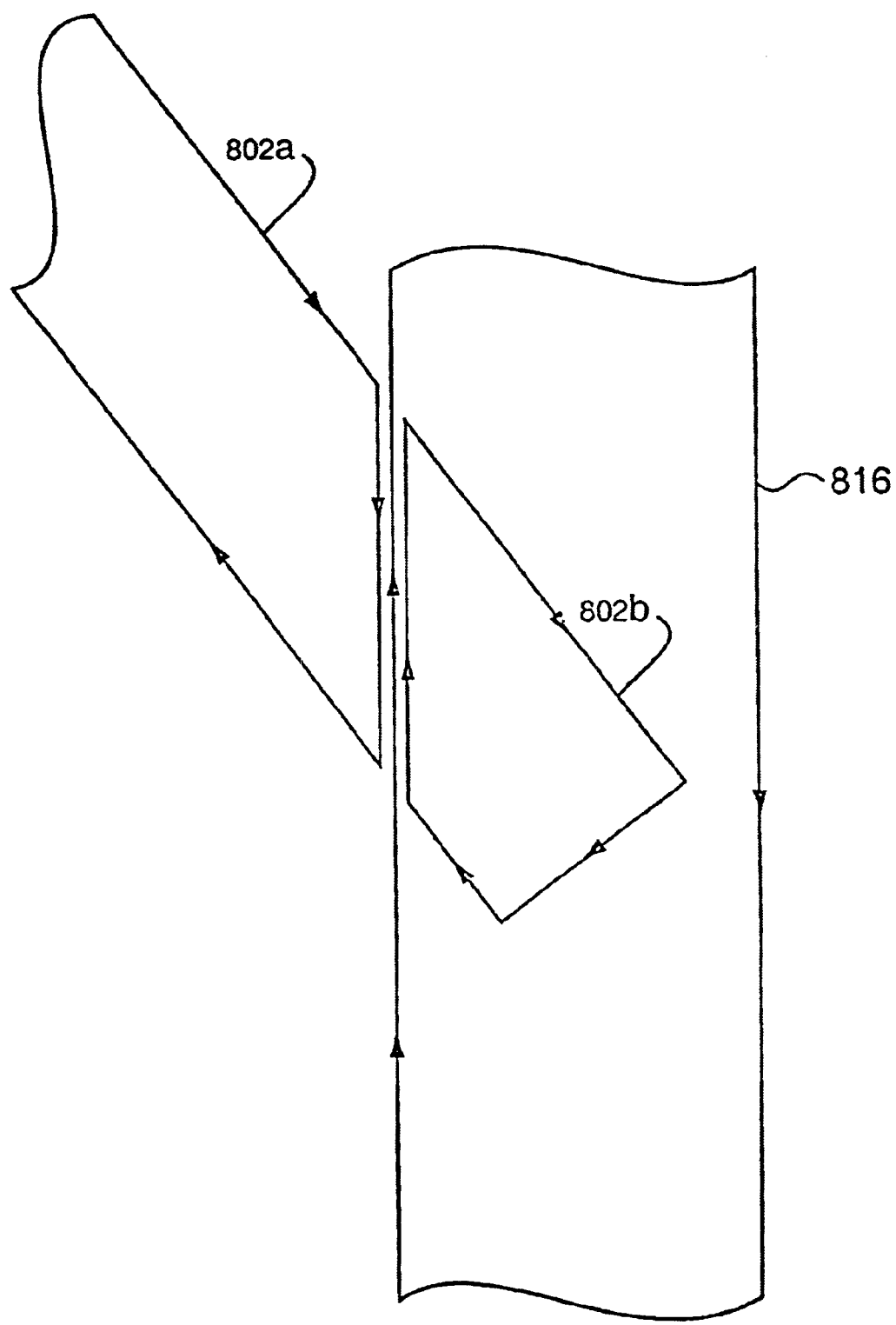
FIG. 9 is an exploded top view of a delta coil and a uniform coil in FIG. 8, consistent with this invention, arranged substantially coplanar.
Figure 9A:
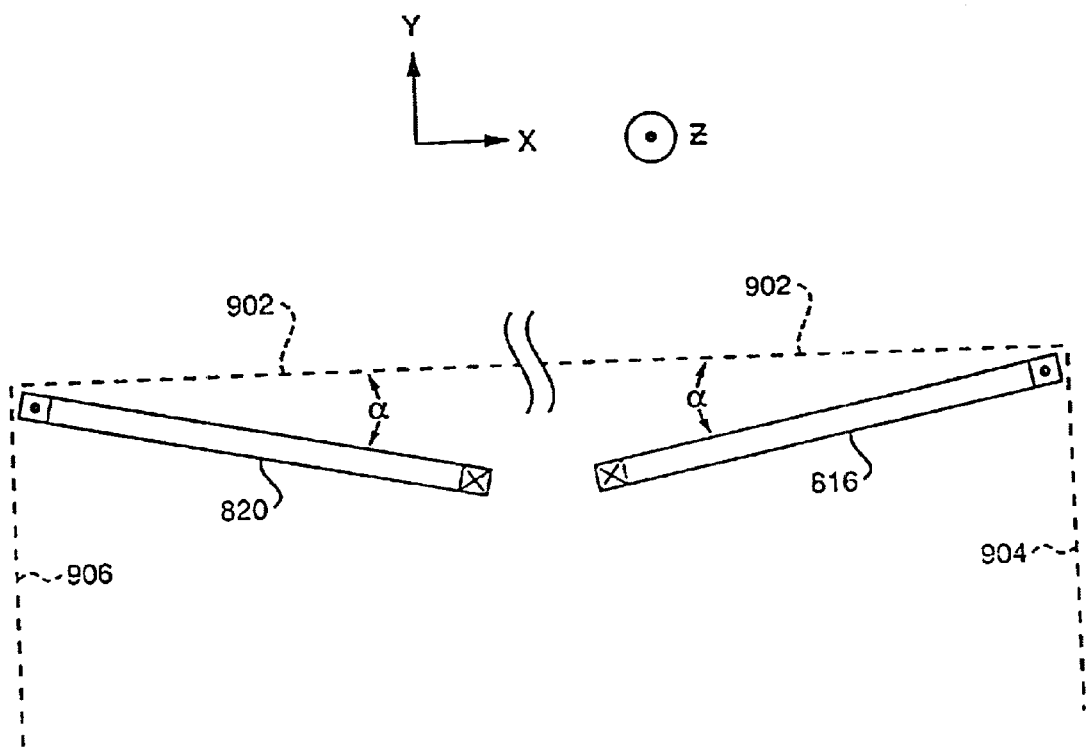
FIG. 9A is an exploded side view of a uniform coil set, consistent with this invention.

FIG. 9A is an exploded side view of a uniform coil set, consistent with this invention. In FIG. 9A, first, second, and third delta coil sets (not shown) are substantially in a plane 902. First uniform coil set 816, 820, in this embodiment is displaced by an angle α from plane 902 as shown. Offset angle α eliminates the need for compensation coils 24 and 26 in FIG. 2A while achieving the same result. Thus, displacing first uniform coil set 816, 820 by angle α cancels undesirable magnetic field components in the Y and Z directions. As a result, uniform coil set 816, 820 generates a substantially uniform X direction field. Second uniform coil set 814, 818 may also be displaced by angle α. It is evident to one of ordinary skill in the art how to calculate angle α necessary to create equivalent correction to eliminate elements 24, 26.

FIG. 9A is an exploded side view of a uniform coil set, consistent with this invention. In FIG. 9A, first, second, and third delta coil sets (not shown) are substantially in a plane 902. First uniform coil set 816, 812, in this embodiment is displaced by an angle α from plane 902 as shown. Offset angle α eliminates the need for compensation coils 24 and 26 in FIG. 2A while achieving the same result. Thus, displacing first uniform coil set 816, 820 by angle α cancels undesirable magnetic field components in the Y and Z directions. As a result, uniform coil set 816, 820 generates a substantially uniform X direction field. Second uniform coil set 814, 818 may also be displaced by angle α. It is evident to one of ordinary skill in the art how to calculate angle α necessary to create equivalent correction to eliminate elements 24, 26.

Figure 10:
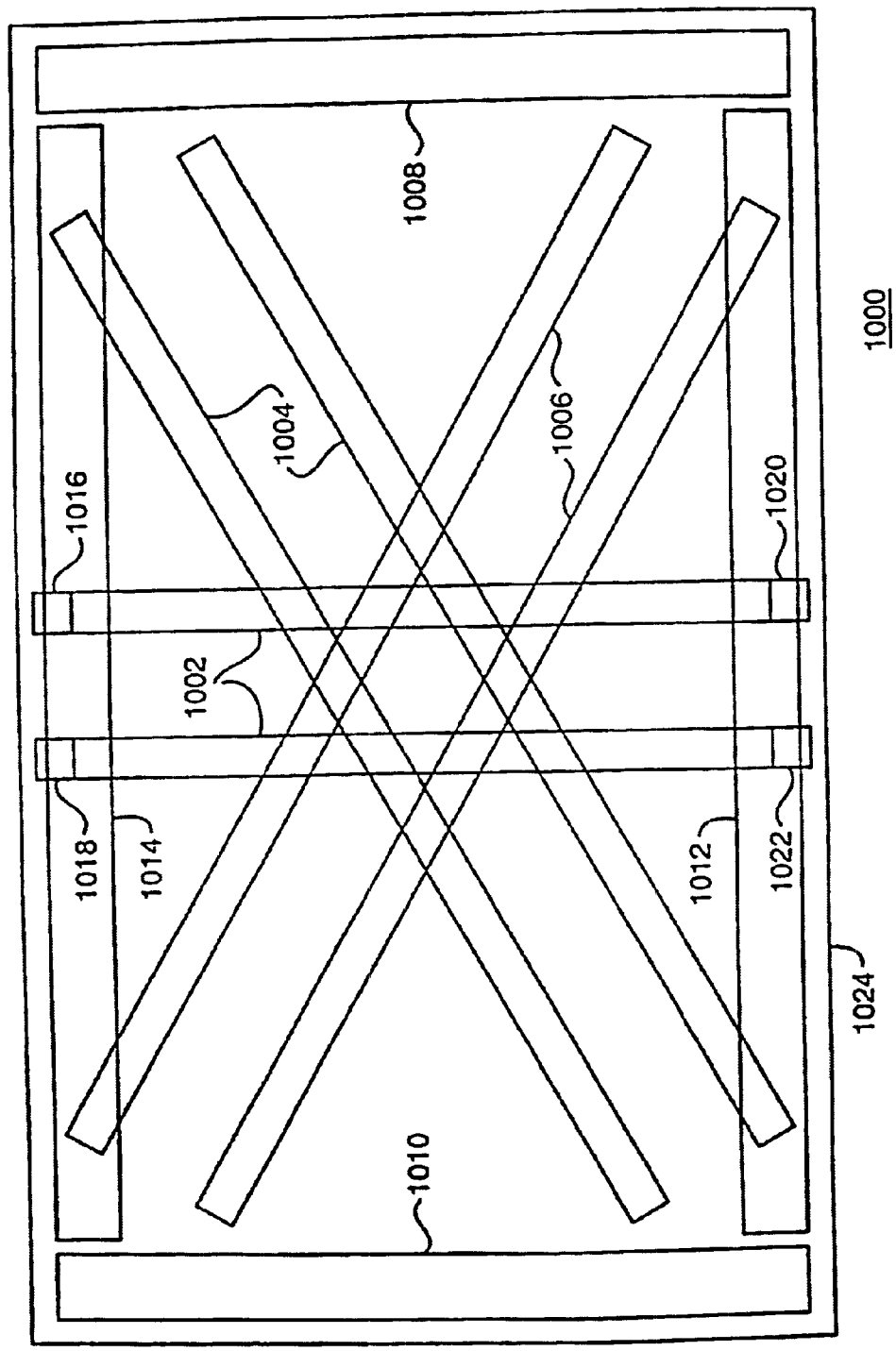
FIG. 10 is a top view of coil sets, consistent with this invention, arranged substantially coplanar for generating magnetic fields.

FIG. 10 is a top view of coil sets, consistent with this invention, arranged substantially coplanar for generating magnetic fields. An arrangement 1000 comprises a first delta coil pair 1002 a second delta coil pair 1004 and a third delta coil pair 1006. First through third delta coil pairs 1002–1004 create gradient fields similar those discussed above with respect to FIG. 3. Arrangement 1000 also comprises a first uniform coil pair 1012–14 and a second uniform coil pair 1008–1010. First and second uniform coil pair 1012–1014, 1008–1010 generate uniform magnetic fields similar to those discussed above with relation to FIGS. 2A and 2C. Arrangement 1000 also comprises a girth coil 1024 that generates a substantially uniform magnetic field similar to the magnetic fields discussed above with respect to FIG. 2B. First delta coil pair 1002, which in this embodiment is shorter than second delta coil pair 1004 and third delta coil pair 1006, contains end correction elements 1018, 1016, 1022, and 1020. End correction elements carry current in the reverse direction to reduce unwanted magnetic field components.

Figure 11:
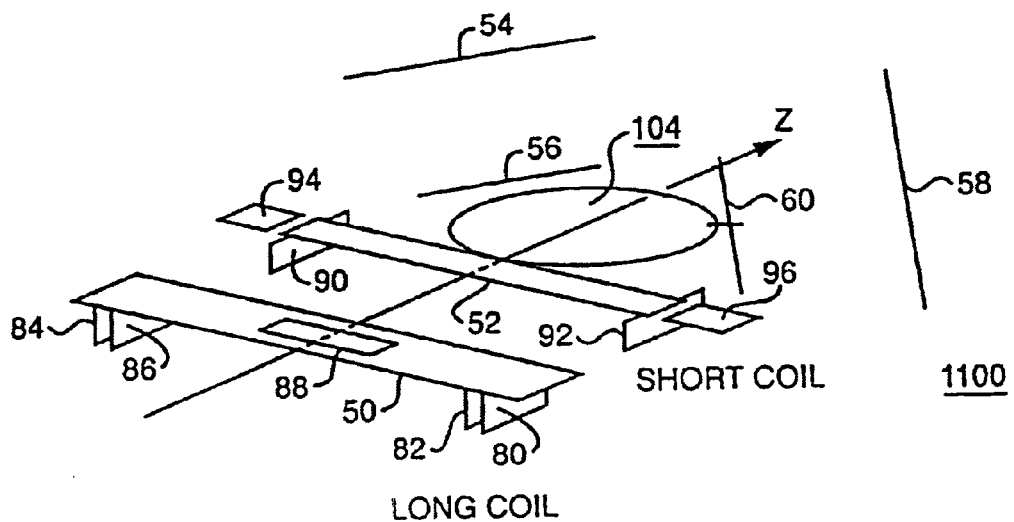
FIG. 11 is a diagram of a top view of a delta coil arrangement relative to an inner circular space.

FIG. 11 is a diagram of a top view of a delta coil arrangement 1100 relative to an inner circular space 104. In arrangement 1100, a short coil 52 is provided with end correction elements 94, 96. Long coil 50 comprises a central compensating or "sucker" coil 88, which carries current in the opposite direction than coil 50 and eliminates some unwanted magnetic field components. Long coil 50 and short coil 52 are modified by compensation coils 80–82, 84–86, 88, 90–94, and 92–96. Long coil 50 and short coil 52 are shown schematically for sets 50–52, but similar configurations likewise exist for coil sets 54–56 and 58–60.

Figure 12:
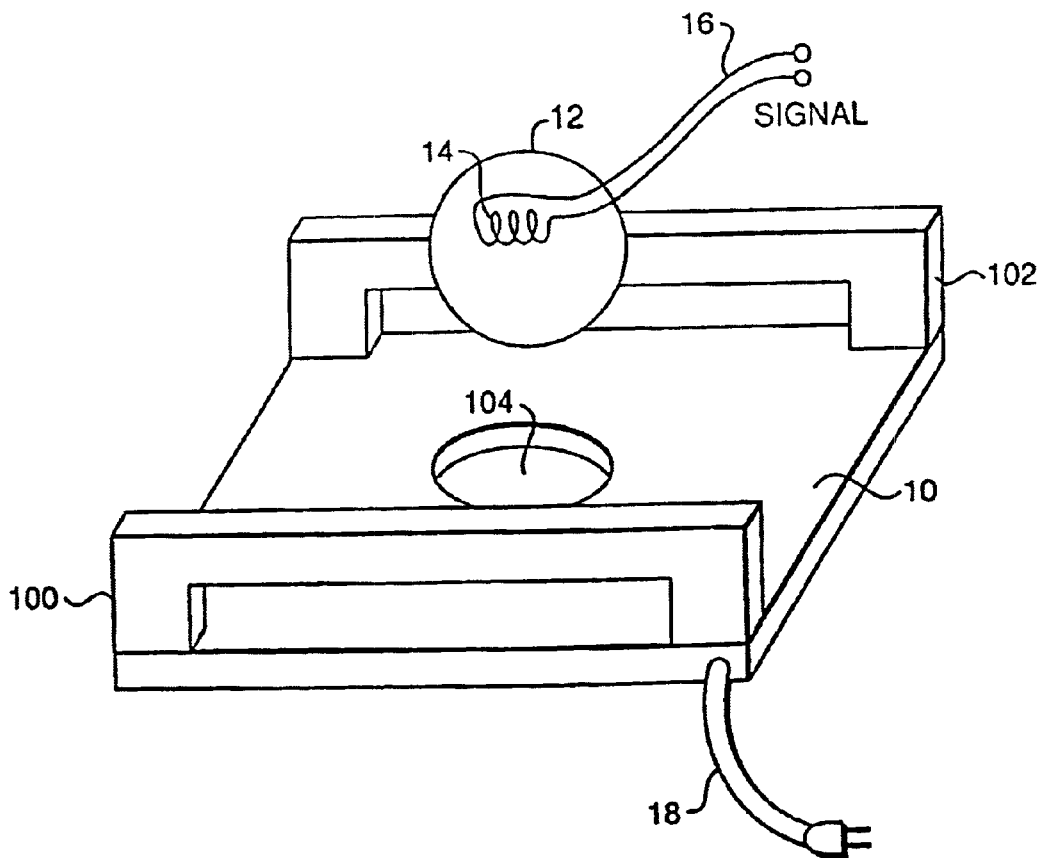
FIG. 12 schematically depicts an examination deck.
Figure 13A:
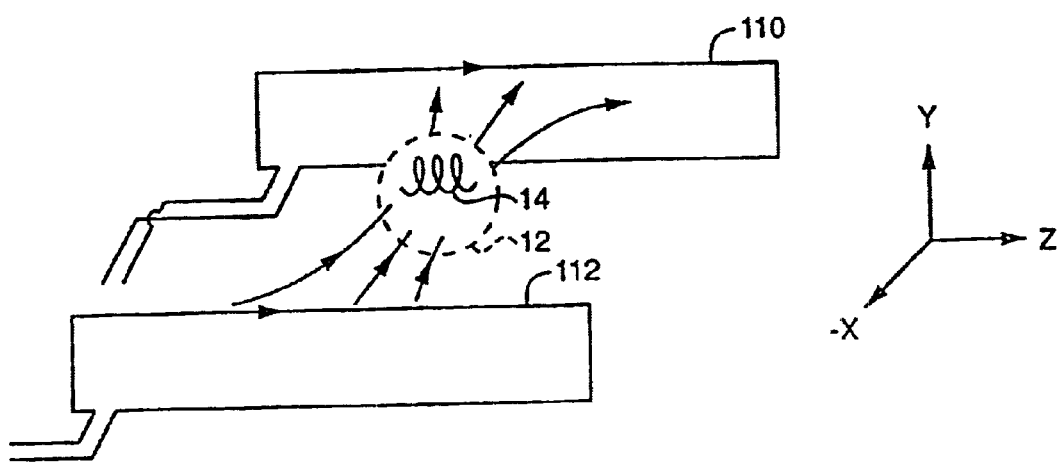
FIGS. 13A, 13B, 13C, and 13D show magnetic field generating coils.
Figure 13B:
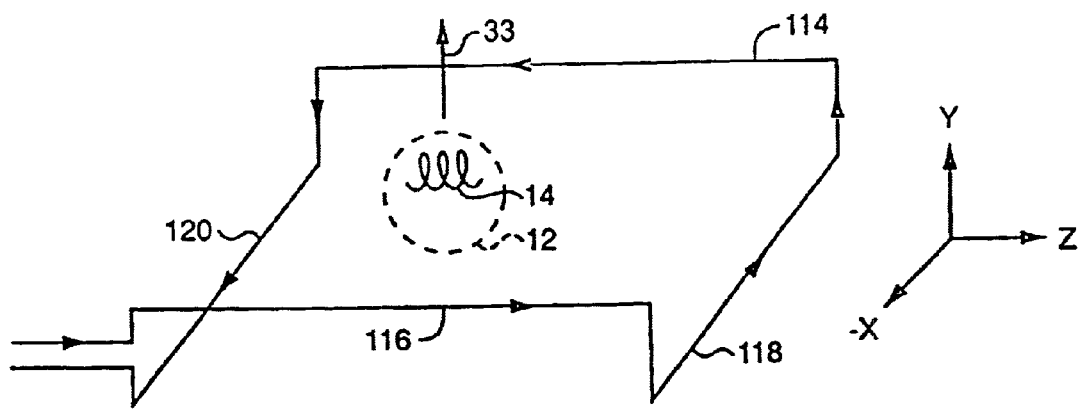
Figure 13C:
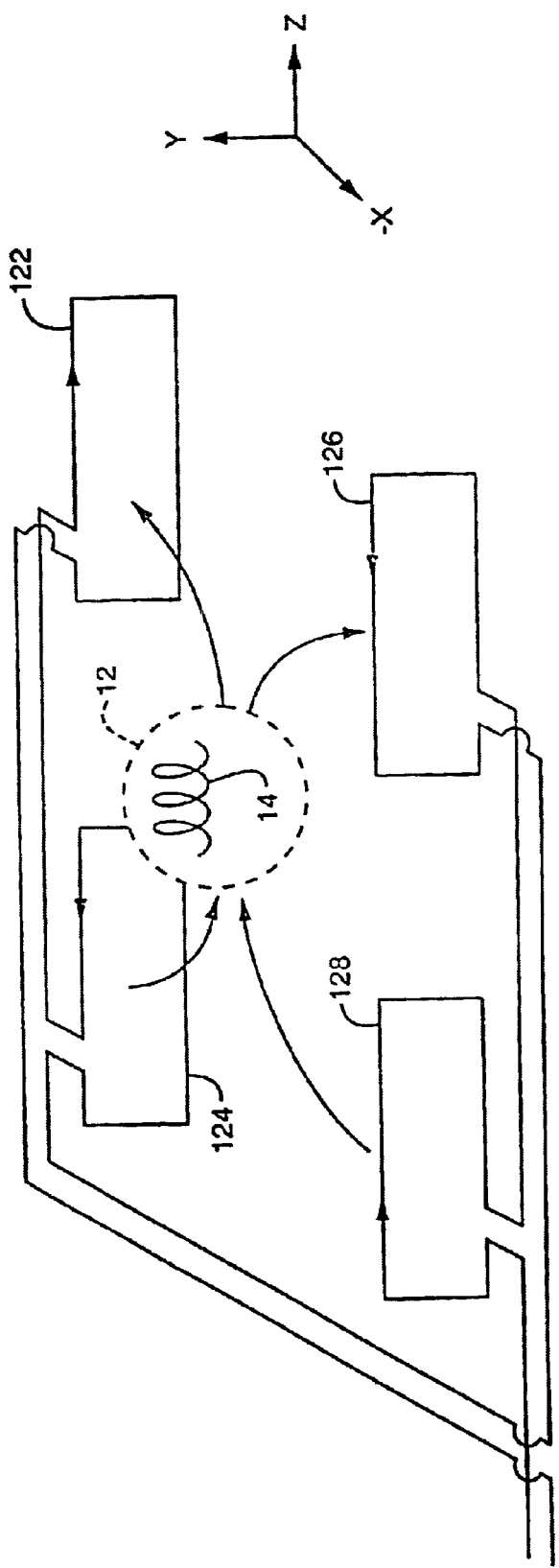
Figure 13D:
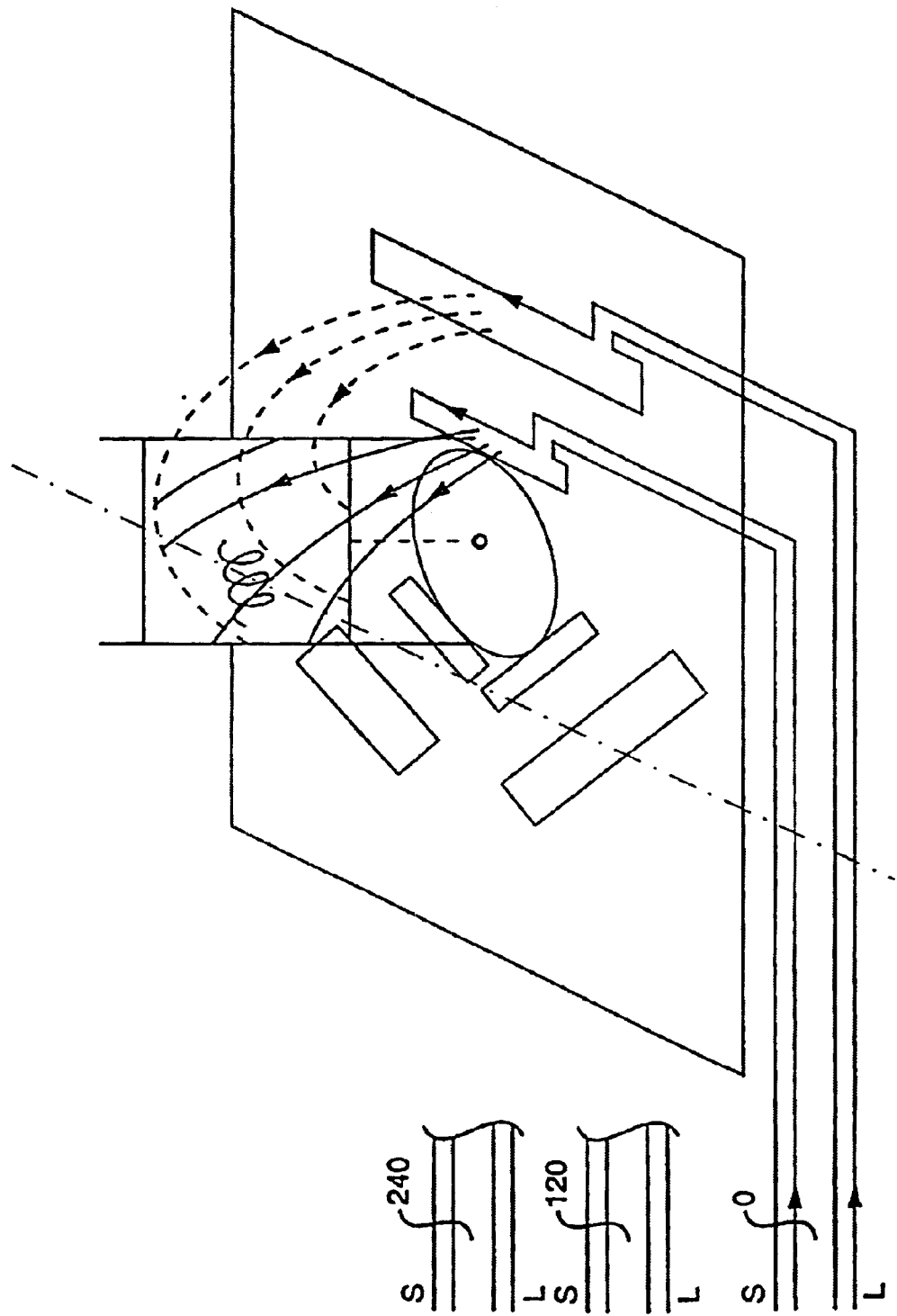

FIG. 12 schematically depicts another examination deck in accordance with another embodiment of the present invention. FIGS. 13A–C are diagrams of unidirectional coils. The assembly for the X direction unidirectional coil set is shown in FIG. 13A and includes two coil elements 110 and 112. Elements 110, 112 project a substantially uniform field in the X direction throughout the navigational domain. FIG. 13B schematically depicts the Y direction unidirectional coils including coil elements 114, 116, 118, and 120. FIG. 13C schematically depicts the Z direction unidirectional coils including coil elements 122–124, and 126–128. FIG. 13D shows the delta coil arrangement used in the railed configuration. The arrangement in FIG. 13D is the same as used in FIG. 3 described above.

Discussion of FIG. 11, 12, 13A, 13B, 13C, and 13D are for illustrative purposes only. See U.S. Pat. No. 5,592,939 for further examples.

Figure 14:
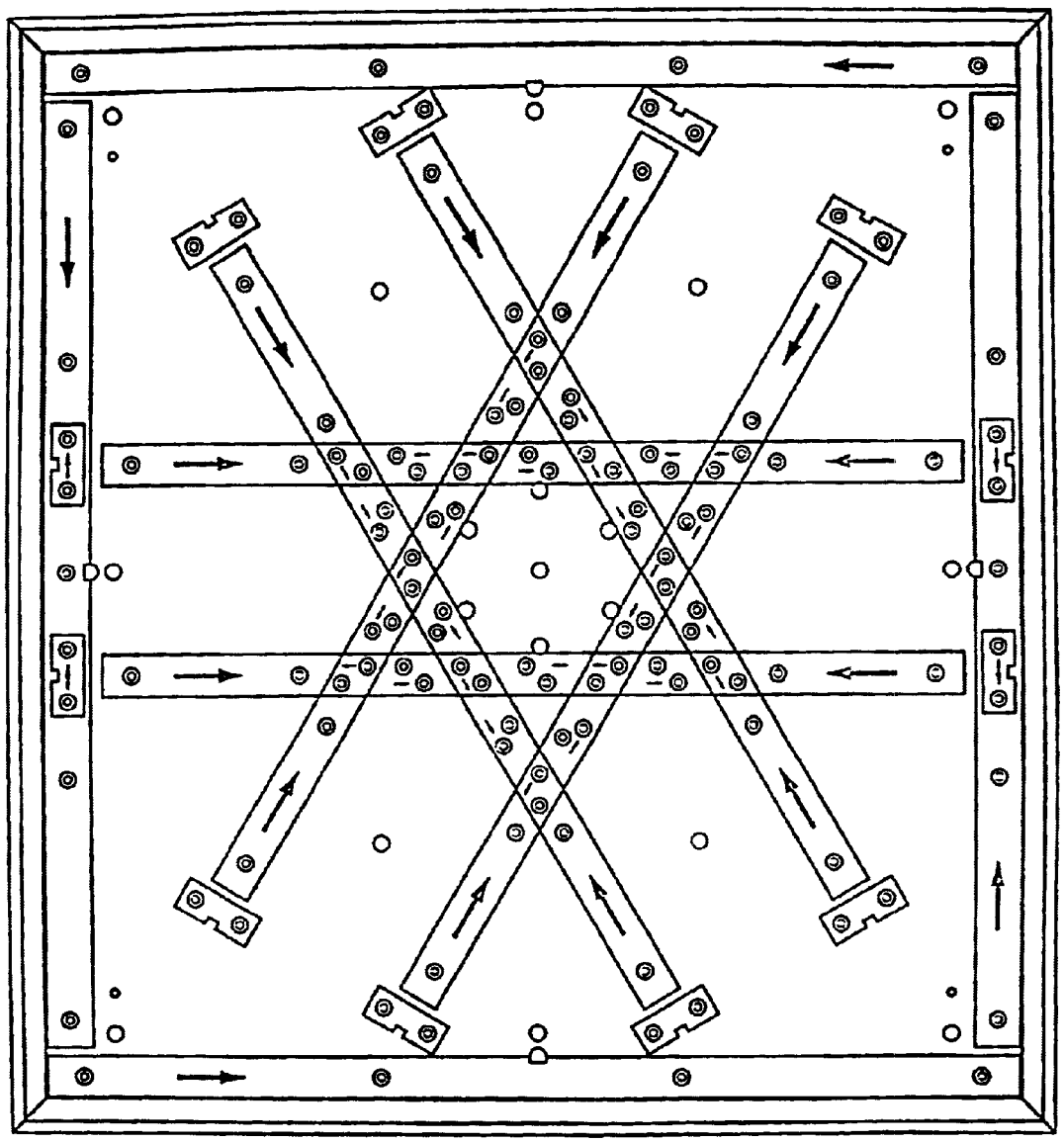
FIG. 14 is an engineering drawing of the coil sets, consistent with this invention, shown in FIG. 5.
Figure 15:
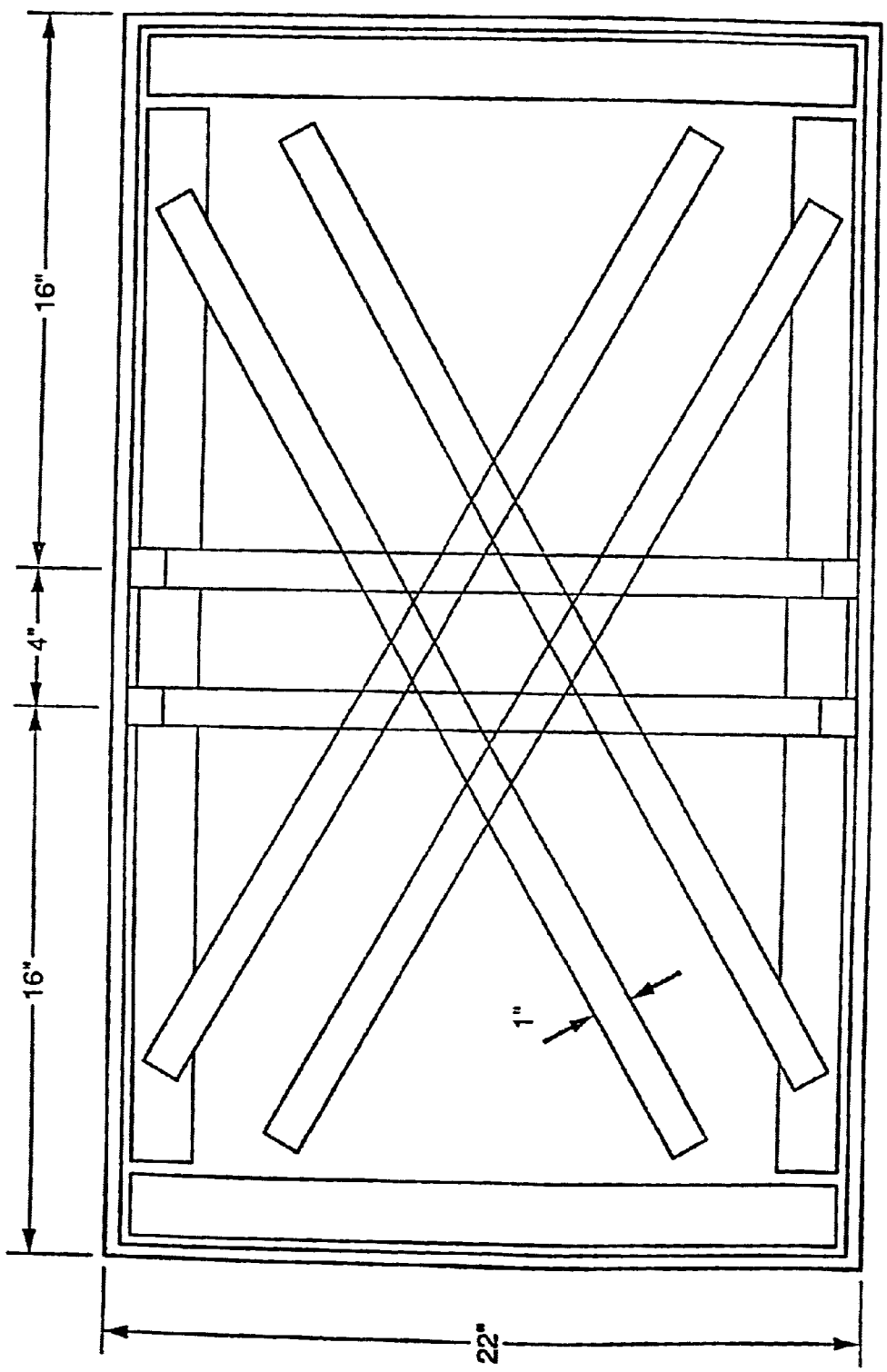
FIG. 15 is an engineering drawing of the coil sets, consistent with this invention, shown in FIG. 10.
Figure 16:
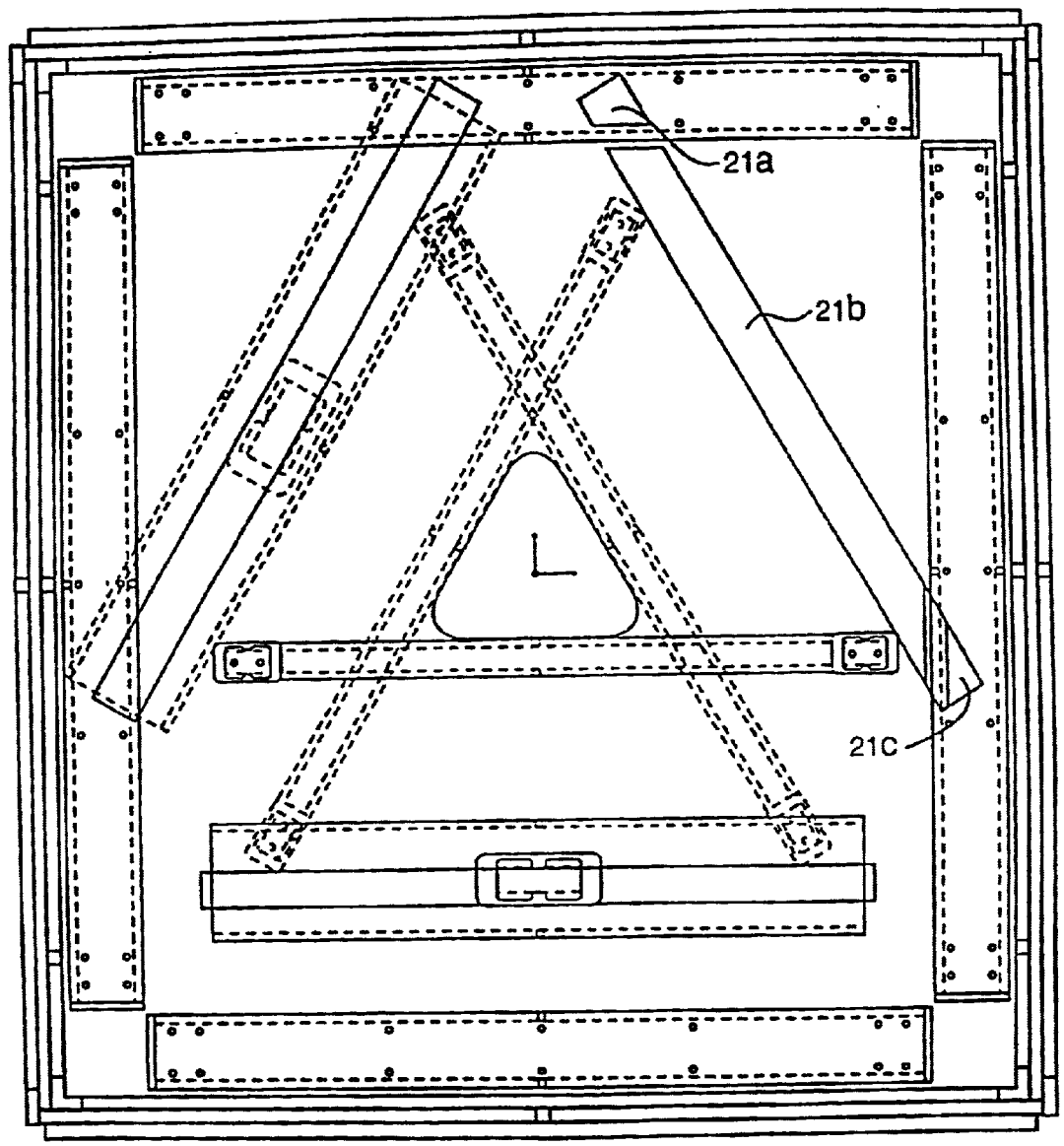
FIGS. 16 and 17 are engineering drawings, consistent with this invention, of the coil sets shown in FIG. 8.
Figure 16:
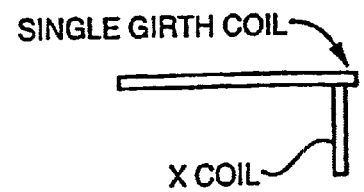
Figure 17:
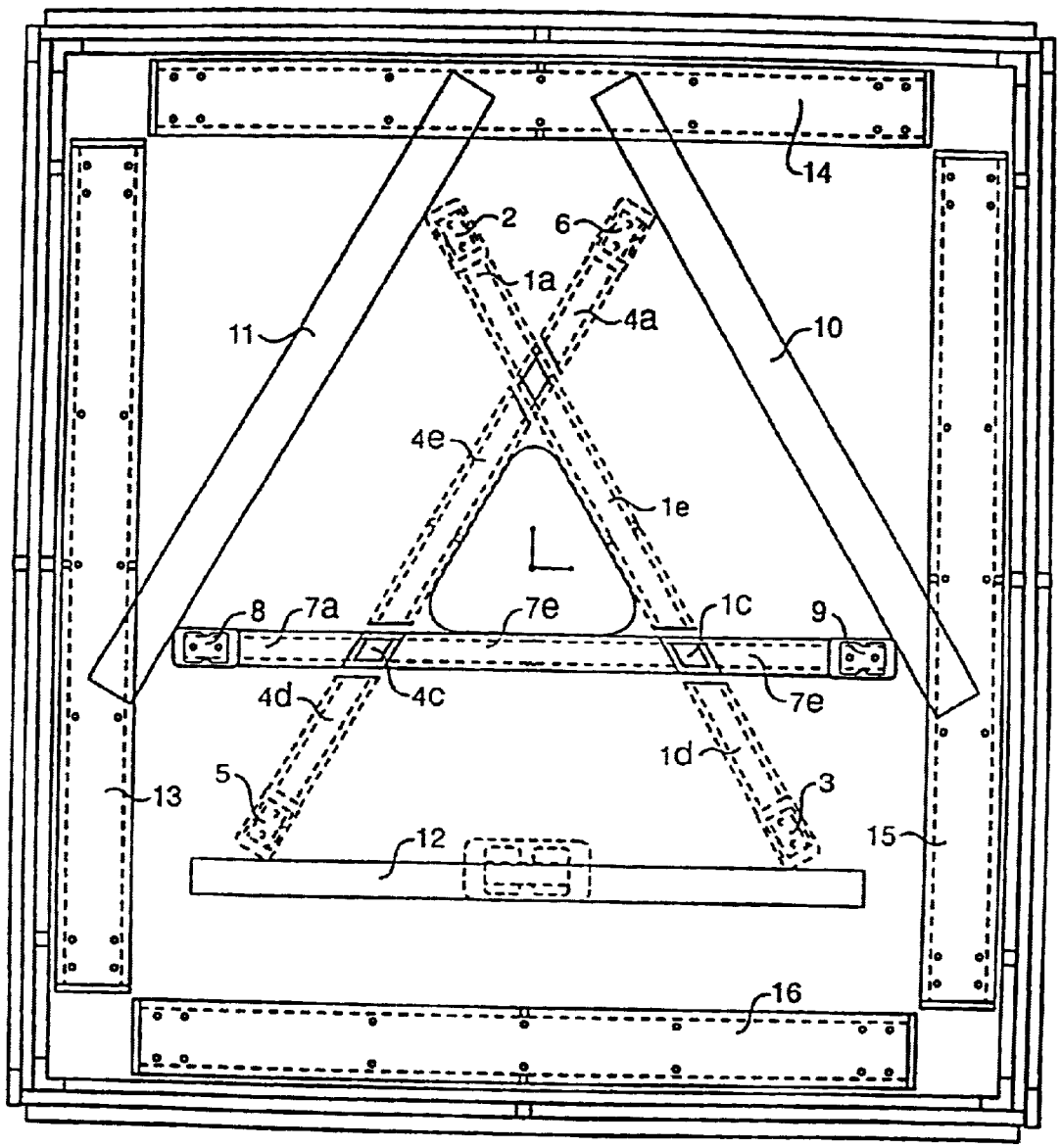
Figure 18:
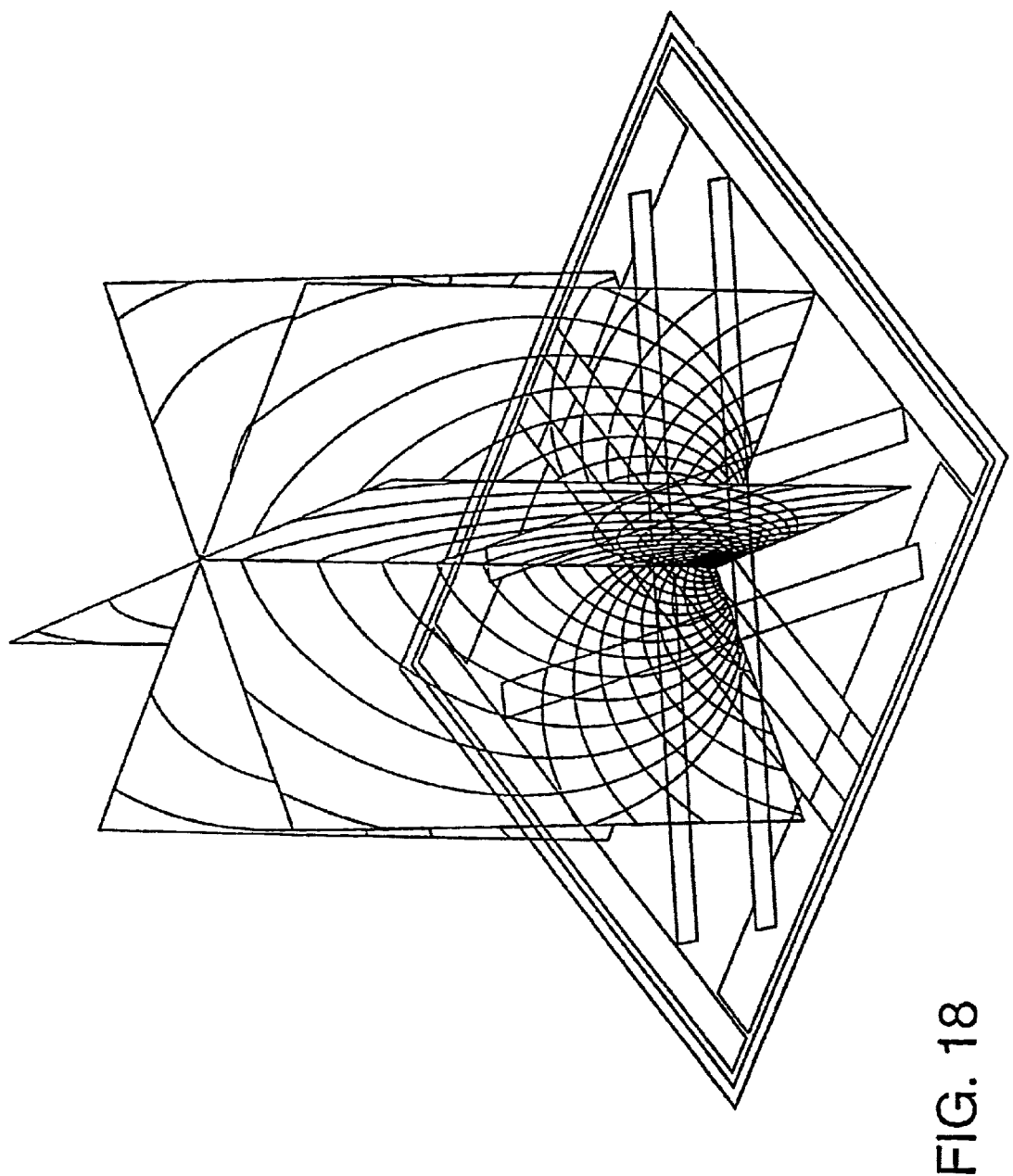
FIG. 18 shows a constant signal pattern for a catheter in a magnetic field generated by the delta coil set of FIG. 10.

FIG. 14 is an engineering drawing of the coil sets, consistent with this invention, shown in FIG. 5. FIG. 15 is an engineering drawing of the coil sets, consistent with this invention, shown in FIG. 10. As shown in FIG. 15, the coils can easily fit onto an operating table that is twenty inches wide and twenty-two inches long. FIGS. 16 and 17 are an engineering drawings, consistent with this invention, of the coil sets shown in FIG. 8. FIG. 18 shows the constant signal pattern for a catheter at $\phi=90$ and $\theta=90$ degrees of a magnetic field generated by a delta coil set in FIG. 10.

Figure 19:
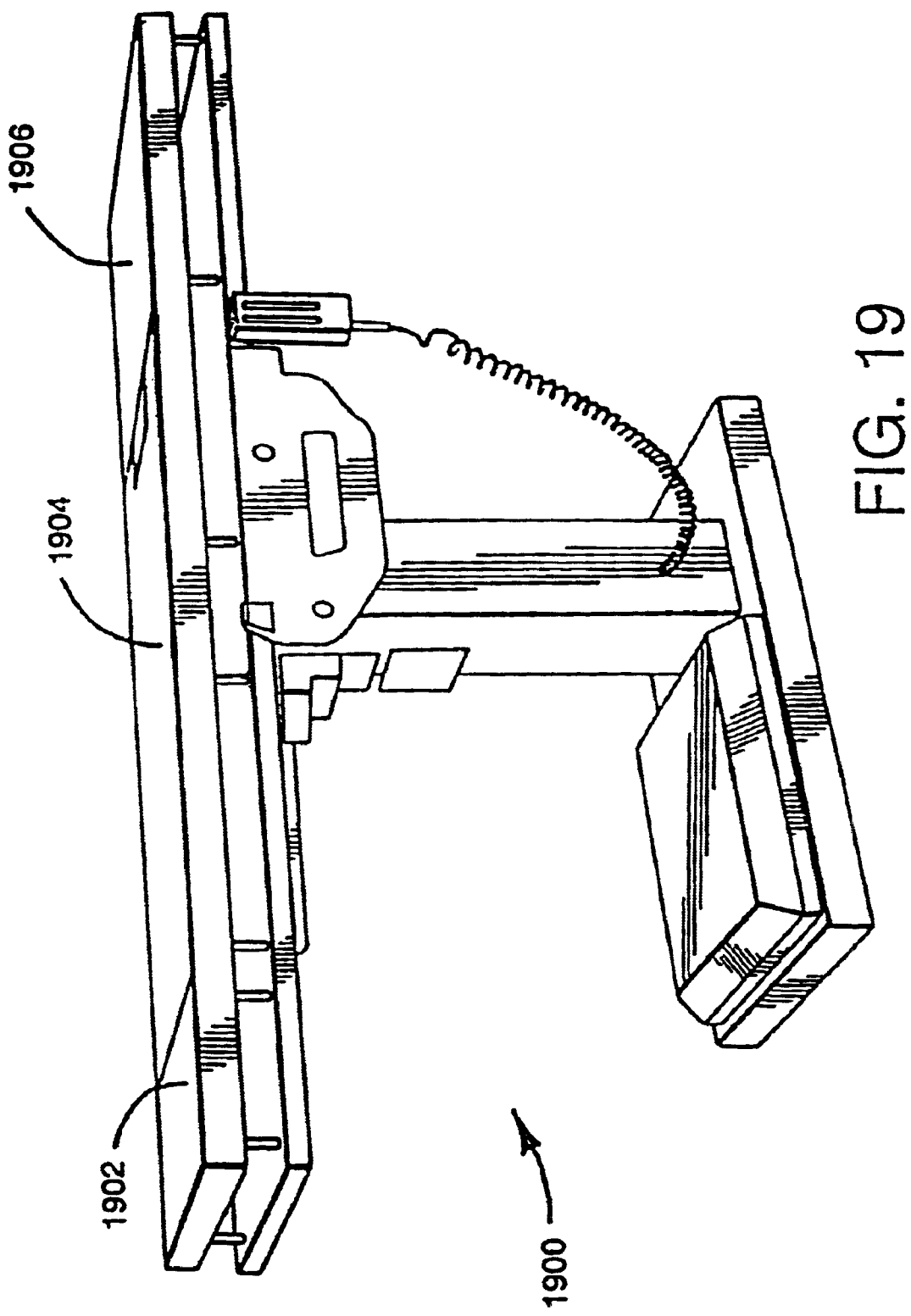
FIG. 19 is a diagram of a surgical table with an integrated examination deck.
Figure 20C:
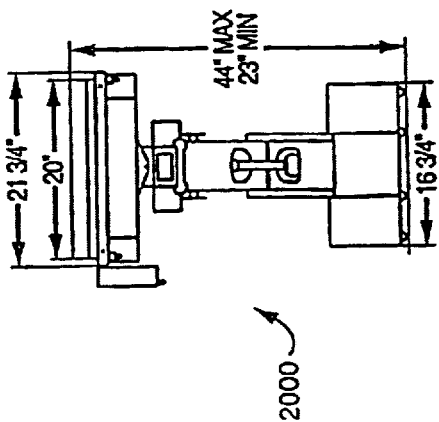
FIG. 20 is a top view, side view, and an end view of an examination deck with an integrated examination deck.
Figure 20A:
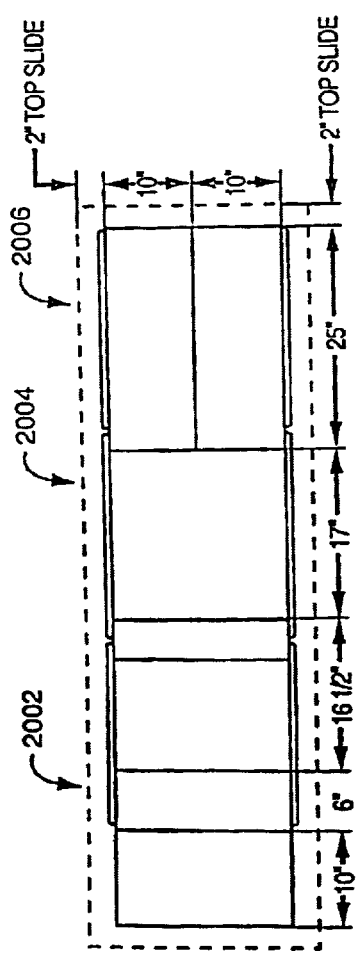
Figure 20B:
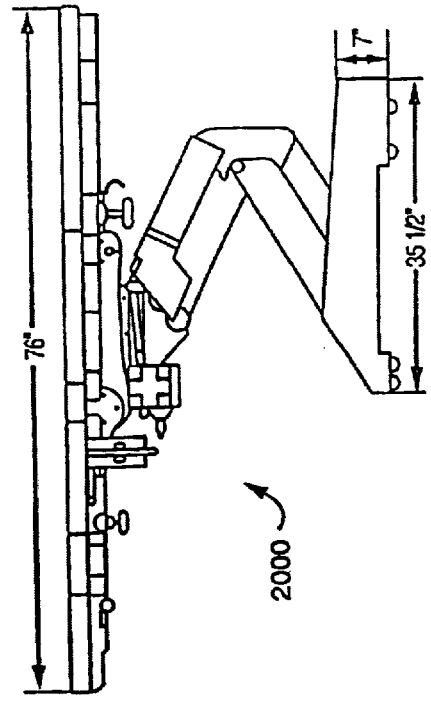

FIG. 19 is a diagram of a surgical table 1900 with an integrated examination deck. The examination deck comprising field generating coils may be integrated at any or all locations 1902, 1904, and 1906. Alternatively, field generating coils may be integrated directly into surgical table 1900 at any or all locations 1902, 1904, and 1906. FIG. 20 is a top view, side view, and an end view of surgical table 2000 with an integrated examination deck. The examination deck comprising field generating coils may be integrated at any or all locations 2002, 2004, and 2006. Alternatively, field generating coils may be integrated directly into surgical at any or all locations 2002, 2004, and 2006.

The invention may be embodied in other specific forms without departing from the spirit or essential characteristics thereof. The present embodiments are therefore to be considered in respects as illustrative and not restrictive, the scope of the invention being indicated by the appended claims rather than by the foregoing description, and all changes which come within the meaning and range of the equivalency of the claims are therefore intended to be embraced therein.

What is claimed is:

1. An apparatus for determining a location of a sensor in a surgical navigation domain, comprising:
   a first magnetic field generator including a first coil set, said first coil set including a first coil that intersects with a second coil;
   a second magnetic field generator including a second coil set, wherein the first and second coil sets are disposed within a common plane; and,
   a processor, configured to receive a plurality of signals, for calculating the location of the sensor from the plurality of signals, wherein the sensor produces the plurality of signals in response to magnetic fields generated by the first and second magnetic field generators.

2. The apparatus according to claim 1, wherein the first coil set includes at least one delta coil pair for generating a gradient magnetic field in the navigation domain.

3. The apparatus according to claim 2, each delta coil pair further including one or more end correction coils, wherein each delta coil pair is electrically coupled to the corresponding end correction coil, and current flows through the end correction coil in a direction opposite of the direction of the current flowing through the corresponding delta coil pair.

4. The apparatus according to claim 1, wherein the second coil set includes at least one uniform coil pair for generating a uniform magnetic field in the navigational domain.

5. The apparatus according to claim 1, wherein the first coil set includes a first delta coil pair longitudinally oriented along a first axis, a second delta coil pair longitudinally oriented along a second axis, and a third delta coil pair longitudinally oriented along a third axis, such that the second axis is rotated within the common plane substantially sixty degrees with respect to the first axis, and the third axis is rotated within the common plane substantially one hundred and twenty degrees with respect to the first axis.

6. The apparatus according to claim 5, wherein each of the first, second and third delta coil pairs lies within the common plane, such that the delta coil pairs intersect one another.

7. The apparatus according to claim 5, wherein each of the first, second and third delta coil pairs includes two or more distinct coil elements, electrically coupled, such that the aggregate of the distinct coil elements produces the corresponding gradient magnetic field.

8. The apparatus according to claim 7, wherein intersecting delta coil pairs share one or more common coil elements.

9. The apparatus according to claim 7, wherein intersecting delta coil pairs include distinct coil elements in an intersecting region where the delta coil pairs overlap.

10. The apparatus according to claim 5, each of the delta coil pairs further including one or more end correction coils, wherein each of the delta coil pairs is electrically coupled to the corresponding end correction coil, and electrical current flows through the end correction coils in a direction opposite of the direction of the current flowing through the corresponding delta coil pair.

11. The apparatus according to claim 5, wherein at least one of the delta coil pairs is characterized by a length different from the length of the other delta coil pairs.

12. The apparatus according to claim 5, wherein each of the delta coil pairs includes:
    a short coil, further including a first end correction element and a second end correction element for reducing unwanted magnetic field components, wherein electrical current flows through the end correction coils in a direction opposite of the direction of the current flowing through the corresponding short coil; and,
    a long coil, further including a central compensating coil for reducing unwanted magnetic field components, wherein electrical current flows through the central compensating coil in a direction opposite of the direction of the current flowing through the corresponding long coil.

13. The apparatus according to claim 5, wherein one or more of the delta coil pairs overlap a coplanar uniform coil pair.

14. The apparatus according to claim 13, wherein each of the one or more overlapping delta coil pairs includes two or more distinct coil elements, electrically coupled, such that the aggregate of the distinct coil elements produces the corresponding gradient magnetic field.

15. The apparatus according to claim 5, wherein said first coil forms part of said first delta coil pair and said second coil forms part of said second delta coil pair.

16. The apparatus according to claim 1 wherein said first coil and said second coil share one or more common coil elements at said intersection.

17. The apparatus according to claim 1, wherein said first coil and said second coil include distinct coil elements at said intersection.

18. An apparatus for determining a location of a sensor in a surgical navigation domain, comprising:
    a first magnetic field generator including at least a first delta coil pair and a second delta coil pair for generating a gradient magnetic field in said navigation domain, the first delta coil pair intersecting with the second delta coil pair, wherein the first and second delta coil pairs are disposed within a first common plane;
    a second magnetic field generator including at least one uniform coil pair for generating a uniform magnetic field in the navigational domain, the at least one uniform coil pair disposed within a second plane, wherein the first plane is offset from the second plane by an offset angle calculated to reduce undesirable uniform field components; and,
    a processor, configured to receive a plurality of signals, for calculating the location of the sensor from the plurality of signals, wherein the sensor produces the plurality of signals in response to magnetic fields generated by the first and second magnetic field generators.

19. An apparatus for determining a location of a sensor in a surgical navigation domain, comprising
    a first magnetic field generator including a common coil;
    a second magnetic field generator including the common coil;
    a processor, configured to receive a plurality of signals, for calculating the location of the sensor, wherein the sensor produces the plurality of signals in response to a first magnetic field generated by the first magnetic field generator and in response to a second magnetic field of a different shape than the first magnetic field generated by the second magnetic field generator wherein said first magnetic field generator includes a first coil and said second magnetic field generator includes a second coil, said first and second coil intersects at said common coil in plane.

20. A method of determining a location of a sensor in a surgical navigation domain, comprising:
    generating a first magnetic field using a first magnetic field generator including a first coil set having a first coil intersecting with a second coil;
    generating a second magnetic field using a second magnetic field generator including a second coil set, wherein the first and second coils are disposed within a common plane;
    calculating the location of the sensor from a plurality of signals, wherein the sensor produces the plurality of signals in response to magnetic fields generated by the first and second generated magnetic fields.

21. The method according to claim 20, wherein generating a first magnetic field further includes generating a gradient magnetic field in said navigation domain using at least one delta coil pair for generating.

22. The method according to claim 20, wherein generating a first magnetic field further includes generating a gradient magnetic field in said navigation domain using two or more distinct coil elements, electrically coupled, such that the aggregate of the distinct coil elements produces the corresponding gradient magnetic fields.

23. The method according to claim 20, wherein generating a first magnetic field further includes generating a gradient magnetic field in said navigation domain using delta coil pairs having one or more end correction coils, wherein each of the delta coil pairs is electrically coupled to the corresponding end correction coil, and electrical current flows through the end correction coils in a direct opposite of the direction of the current flowing through the corresponding delta coil pair.

24. A method of determining a location of a sensor in a surgical navigation domain, comprising:
    generating a gradient magnetic field in said navigation domain using a first magnetic field generator including at least a first delta coil pair and a second delta coil pair disposed within a first common plane and intersecting one another;

generating a uniform magnetic field in the navigational domain using a second magnetic field generator including at least one uniform coil pair, the at least one uniform coil pair disposed within a second plane, wherein the first plane is offset from the second plane by an offset angle calculated to reduce undesirable uniform field components; and, calculating the location of the sensor from a plurality of signals, wherein the sensor produces the plurality of signals in response to magnetic fields generated by the first and second generated magnetic fields.

25. A method of determining a location of a sensor in a surgical navigation domain, the method comprising:

generating a first magnetic field using a magnetic field generator including a common coil;

generating a second magnetic field of a different shape than the first magnetic field using a second magnetic field generator including the common coil;

calculating the location of the sensor from a plurality of signals, wherein the sensor produces the plurality of signals in response to magnetic fields generated by the first and second magnetic field generators wherein said first magnetic field generator includes a first coil and said second magnetic field generator includes a second coil, said first and second coil intersects at said common coil in plane.

26. An apparatus for determining a location of a sensor in a surgical navigation domain, comprising:

a first magnetic field generator including a common coil in a plane;

a second magnetic field generator including the common coil in said plane;

a processor, configured to receive a plurality of signals, for calculating the location of the sensor, wherein the sensor produces the plurality of signals in response to a first magnetic field generated by the first magnetic field generator and in response to a second magnetic field of a different shape than the first magnetic field generated by the second magnetic field generator, wherein said first magnetic field generator includes a first coil and said second magnetic field generator includes a second coil where said first coil intersects said second coil at the common coil in said plane.

27. A method of determining a location of a sensor in a surgical navigation domain, the method comprising:

generating a first magnetic field using a magnetic field generator having a first coil and including a common coil in a plane;

generating a second magnetic field of a different shape than the first magnetic field using a second magnetic field generator having a second coil and including the common coil in said plane;

positioning the first coil relative to the second coil where the first coil intersects the second coil at the common coil in said plane;

calculating the location of the sensor from a plurality of signals, wherein the sensor produces the plurality of signals in response to magnetic fields generated by the first and second magnetic field generators.

28. An apparatus for determining a location of a sensor in a surgical navigation domain, comprising:

a first magnetic field generator including at least a first coil;

a second magnetic field generator including at least a second coil, said first coil intersecting with said second coil, wherein the first and second coils are disposed within a common plane; and a processor configured to receive a plurality of signals, for calculating the location of the sensor from the plurality of signals, wherein the sensor produces the plurality of signals in response to the magnetic fields generated by the first and second magnetic field generators.

29. An apparatus for determining a location of a sensor in a surgical navigation domain, comprising:

a first coil operable to generate a first magnetic field;

a second coil operable to generate a second magnetic field, said first coil intersects through said second coil within a common plane; and a processor configured to receive a plurality of signals, for calculating the location of the sensor from the plurality of signals, wherein the sensor produces the plurality of signals in response to the magnetic fields generated by the first and second coils.

30. The apparatus according to claim 29 wherein said first coil and said second coil share one or more common coil elements at said intersection.

31. The apparatus according to claim 29, wherein said first coil and said second coil include distinct coil elements at said intersection.

* * * * *